United States Patent
Pedersen et al.

(10) Patent No.: US 7,056,730 B2
(45) Date of Patent: Jun. 6, 2006

(54) EXPRESSION OF HETEROLOGOUS GENES FROM AN IRES TRANSLATIONAL CASSETTE IN RETROVIRAL VECTORS

(75) Inventors: Finn Skou Pedersen, Aarhus V (DK); Thomas Jesperson, Koebenhavn N (DK); Mogens Duch, Risskov (DK)

(73) Assignee: Aarhus University, Aarhus C (DK)

( * ) Notice: Subject to any disclaimer, the term of this patent is extended or adjusted under 35 U.S.C. 154(b) by 292 days.

(21) Appl. No.: 10/146,483

(22) Filed: Oct. 26, 2001

(65) Prior Publication Data

US 2003/0157718 A1    Aug. 21, 2003

Related U.S. Application Data

(63) Continuation-in-part of application No. 10/129,391, filed as application No. PCT/EP00/03903 on Apr. 29, 2000.

(30) Foreign Application Priority Data

Apr. 29, 1999    (DK) ................................ 1999 00584

(51) Int. Cl.
*C12N 15/867*    (2006.01)

(52) U.S. Cl. .................................................. 435/320.1

(58) Field of Classification Search ............. 435/320.1, 435/325, 456; 536/23.72; 514/44; 935/320.1, 935/325

See application file for complete search history.

(56) References Cited

U.S. PATENT DOCUMENTS 5,925,565 A      7/1999  Berlioz et al.
6,410,313 B1 *   6/2002  Kasahara et al. ........ 435/320.1

FOREIGN PATENT DOCUMENTS

WO    WO 93/03143    *  2/1993

OTHER PUBLICATIONS

Murakami et al., Gene, 202: 23-29 (1997).*
Jespersen et al., Gene, vol. 293 (2), pp. 227-235 (1999).*

* cited by examiner

*Primary Examiner*—Nancy Vogel
(74) *Attorney, Agent, or Firm*—Jonathan Myers; Andrew Wilford

(57) ABSTRACT

The present invention relates to a retroviral vector which expresses a gene, e.g. for therapeutic use and/or of viral origin, under the translational control of an internal ribosomal entry site (IRES) resulting in the efficient translation of said gene.

28 Claims, 3 Drawing Sheets

Figure 1A:
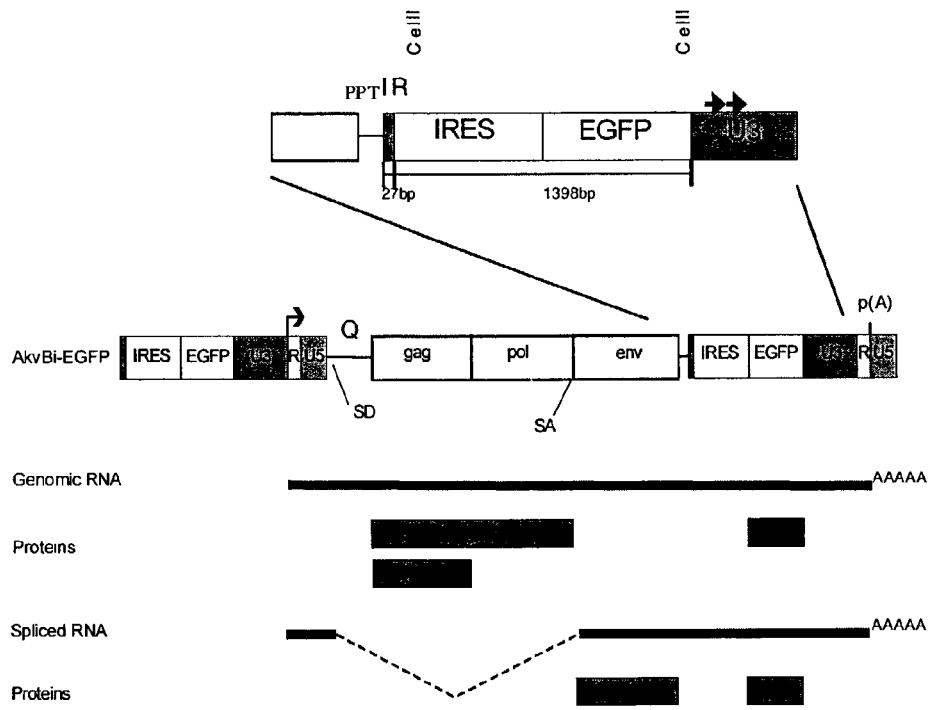

FIG.: 2
Leader sequences from the termination of the IRES to the start codon of the operably linked genes

| Vector | AUG codon: #10 | #11 | sequence list: # |
|---|---|---|---|
| EMCV (wt) | AAACACG ATGATAAT------------------------------------------------------- | ATGGCC | SeqIDNo:11 |
| Bi-zeo-neo | AAACACG ATTGCCGCGTGTGGCCTCGAACACCGAGCGACCCTGCAGCCAAT--------- | ATGGGA | SeqIDNo:3 |
| AkvBi-EGFP | AAACACG ATTGCCGCGTGTGGCCTCGAACACCGAGCGACCCTGCAGCCGCGGTCGAC- | ATGGTG | SeqIDNo:6 |
| Bi-zeo-env | AAACACG CGGCCGCC----------------------------------------------------------- | ATGGAT | SeqIDNo:7 |
| Bi-neo-env | AAACACG ATTGCCGCGTGCGGCCGCTAACACTCCGGAGCTCGAGCCAAT---------- | ATGGAT | SeqIDNo:8 |
| IRES-EGFP #2 | AAACACG ATGATAAGCTTGCCACAACCCGGGATCCACCGGTCGCCACC----------- | ATGGTG | SeqIDNo:9 |
| IRES-EGFP #3 | AAACACG ATAATACC------------------------------------------------------------- | ATGGTG | SeqIDNo:10 |

Fig 3

| Name | Proviral genome structure | RNA genome size | Titer (CFU/ml) G418 | Titer (CFU/ml) G418 + MAb |
|---|---|---|---|---|
| IRES-EFGP | gag pol env IRES-EGFP | 10300 nt | 0 | 0 |
| Bi-zeo-neo | zeo IRES-neo | 2910 nt | 5x10(7) | 1x10(7) |
| Akv wild type | gag pol env | 8500 nt | 0 | 0 |
| AkvBi-neo | gag pol env IRES-neo | 9900 nt | 6x10(7) | 1x10(7) |
| Mega 1 kb +/- | gag pol env 1 kb λ IRES-neo | 10900 nt | 2x10(4)/3x10(4) | 1x10(5)/1x10(5) |
| Mega 2 kb +/- | gag pol env 2 kb λ IRES-neo | 11900 nt | 1x10(2)/1x10(3) | 1x10(2)/4x10(3) |
| Mega 3 kb + | gag pol env 3 kb λ IRES-neo | 12900 nt | 3x10(1) | 1x10(1) |
| Mega 4 kb - | gag pol env 4 kb λ IRES-neo | 13900 nt | 2x10(2) | 1x10(2) |
| Mega-pol 1 kb | Gag pol 1 kb λ env IRES-neo | 10900 nt | 1x10(6) | 1x10(6) |
| Mega-pol 3 kb | Gag pol 3 kb λ env IRES-neo | 12900 nt | 4x10(3) | 1x10(3) |
| Deletion Afl II (1.5 kb) | IRES-neo | 12400 nt | 1x10(2) | 4x10(1) |
| Deletion Afl II-Bst EI (5 kb) | IRES-neo | 8900 nt | 1x10(1) | 2x10(1) |

SEQUENCE LISTING

<160> NUMBER OF SEQ ID NOS: 15

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 1
caagcttagc ggccgccccc taacgttact g                       31

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 2
tatgctaagc tcgactcaga agaactcgtc aag                     33

<210> SEQ ID NO 3
<211> LENGTH: 47
<212> TYPE: DNA
<213> ORGANISM: Artificial Sequence
<220> FEATURE:
<223> OTHER INFORMATION: Description of Artificial Sequence:
      spacer sequence

<400> SEQUENCE: 3
attgccgcgt gtggcctcga acaccgagcg accctgcagc caatatg      47

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence:primer -continued

```
<400> SEQUENCE: 4
gatcgcttag ctgcagatgc atggcccatg cggccgcccc ct                42

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence:primer

<400> SEQUENCE: 5
atgactgcag gctaagccat atgacgcgta cggccgcttt acttgacagc          50

<210> SEQ ID NO 6
<211> LENGTH: 53
<212> TYPE: DNA
<213> ORGANISM: Artificial Sequence
<220> FEATURE:
<223> OTHER INFORMATION: Description of Artificial Sequence:
      spacer sequence

<400> SEQUENCE: 6
attgccgcgt gtggcctcga acaccgagcg accctgcagc cgcggtcgac atg      53

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence:
      spacer sequence

<400> SEQUENCE: 7
aaacacgcgg ccgcc                                                15

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence:
      spacer sequence

<400> SEQUENCE: 8
aacacgattg ccgcgtgcgg ccgctaacac tccggagctc gagccaat            48

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence:
      spacer sequence

<400> SEQUENCE: 9
aaacacgatg ataagcttgc cacaacccgg gatccaccgg tcgccacc            48

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence:
      spacer sequence

<400> SEQUENCE: 10
```
aaacacgata atacc                                                    15

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence:
      spacer sequence

<400> SEQUENCE: 11
aaacaagatg ataat                                                    15

<210> SEQ ID NO 12
<211> LENGTH: 14
<212> TYPE: DNA
<213> ORGANISM: Artificial Sequence
<220> FEATURE:
<223> OTHER INFORMATION: Description of Artificial Sequence:
      5 prime of PL of AENGFMK2

<400> SEQUENCE: 12
cacgggaata aaag                                                     14

<210> SEQ ID NO 13
<211> LENGTH: 68
<212> TYPE: DNA
<213> ORGANISM: Artificial Sequence
<220> FEATURE:
<223> OTHER INFORMATION: Description of Artificial Sequence:
      3 prime of PL of AENGFMK2

<400> SEQUENCE: 13
cttaagacaa tagaagattg taaatcacgt gaataaaaga ttttattcag tttacagaaa    60
gagggggg                                                            68

<210> SEQ ID NO 14
<211> LENGTH: 11
<212> TYPE: DNA
<213> ORGANISM: Artificial Sequence
<220> FEATURE:
<223> OTHER INFORMATION: Description of Artificial Sequence:
      5 prime of IRES cassette in AKENGFML

<400> SEQUENCE: 14
cacgggaata a                                                        11

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence:
      3 prime of PL in AKENGFML

<400> SEQUENCE: 15
aagattttat tcagtttaca gaaagagggg gg                                 32

EXPRESSION OF HETEROLOGOUS GENES FROM AN IRES TRANSLATIONAL CASSETTE IN RETROVIRAL VECTORS

CROSS REFERENCE TO RELATED APPLICATIONS

This application is a continuation-in-part of Ser. No. 10/129,391 filed 14 Oct. 2003 which is the U.S. National Phase of PCT/EP00/03903 filed 29 Apr. 2000 claiming the priority of Danish Patent Application PA 1999 00584 filed 29 Apr. 1999.

The present invention relates to a retroviral vector which expresses a gene, e.g. for therapeutic use and/or of viral origin, under the translational control of an internal ribosomal entry site (IRES) resulting in the efficient translation of said gene.

BACKGROUND OF THE INVENTION

Retroviruses have the capacity to infect a wide variety of cells. Beside this, retroviruses transfer their genes from a producer cell to a target cell as a genomic RNA transcript. This genomic RNA is after infection and reverse transcription integrated into the DNA genome of the target cell. For propagation of infectious virus all replication-competent retroviruses encode as essential genes the so-called gag, pol and env genes that are transcribed from the transcription-regulatory elements contained in the U3-region of the 5'LTR. This transcription starts at the border of the U3- to the R-region of the 5'LTR and the mature transcript finishes at the polyadenylation site at the end of the R-region in the 3'LTR. The resulting RNA transcripts comprise full-length as well as spliced retroviral RNA. The 5'-end of the full-length as well as of the spliced retroviral RNA is modified by addition of a so-called capping group. This structure is important for the attachment of ribosomes and thereby for the translation of the RNA. Translation requires besides this binding signal for a ribosome a so-called open-reading-frame ORF, i.e. a DNA or RNA sequence between an ATG/AUG translation start signal and a termination codon. In normal retroviruses RNA transcripts comprise only one ORF (so-called monocistronic RNA). This monocistronic RNA is capped and translation of the ORF starts at the first translation-start-codon (e.g. ATG) following the capping group and stops at a stop-codon. Consequently, any coding region downstream of said stop-codon wont be translated into a protein. An example for a spliced and capped RNA transcript coding for a single protein is the RNA coding for env. Other essential retroviral proteins, such as e.g. the integrase, reverse transcriptase, protease and capsid protein may be translated as one polypeptide from the capped, full-length RNA transcript. After translation, this polypeptide is proteotytically processed to the different proteins. Hence, this RNA is still monocistronic.

In further developments retroviral vectors have been constructed, which comprise a cassette consisting of a translational control element preceding a heterologous gene (44; 3; 45; 26). In these cases, translation of the one ORF, which is closest to the capping group, starts—as described above—at the first translation-start-codon (ATG or AUG) following the capping group and stops at a stop-codon. For the translation of any further ORF encoded by such a retroviral RNA transcript an additional translational control element, e.g. an internal ribosome entry site (IRES) is necessary.

The term "internal ribosome entry site" (IRES) defines a sequence motive which promotes attachment of ribosomes to that motive on internal mRNA sequences. Furthermore, all factors needed to efficiently start translation at the AUG-start-codon following said IRES attach to this sequence motive. Consequently, an mRNA containing a sequence motive of a translation control element, e.g. IRES, results in two translational products, one initiating from the 5'end of the mRNA and the other by an internal translation mechanism mediated by IRES.

Accordingly, the insertion of a translational control element, such as IRES, operably linked to an ORF into a retroviral genome allows the translation of this additional ORF from a viral RNA transcript. Such RNA transcripts with the capacity to allow translation of two or more ORF are designated bi- or polycistronic RNA transcripts, respectively.

A retroviral vector is characterised by the ability to harbour a heterologous nucleotide sequence in addition to the vector sequence and to transfer said sequence into a receipient. However, for the following reasons, the replication competence of the retrovirus is often lost when a nucleotide sequence is added into the vector. Most retroviruses are adapted in a way that they contain as little RNA as possible and, therefore, contain only essential genes. This is especially true for the simple retroviruses, such as MMTV and MLV, which basically contain only genes encoding virion proteins. Accordingly, insertion of a heterologous sequence into any gene and thereby the inactivation of said viral gene, results in the loss of the replication competence. Additionally, as described above, the RNA-transcripts mostly encode more than one protein, wherein the nucleotide sequences coding for the different proteins sometimes overlap. Hence, the heterologous sequence can also not be added in between of two genes without destroying a coding region. Furthermore, it is known that the nucleotide sequence, which can be efficiently replicated by the retroviral replication machinery, is highly limited in its length, i.e., regularly genes of the viral genome have to be deleted, to have "enough space" for the heterologous sequence, that is added. The deletion of viral sequences again results in the loss of the replication competence. Finally, the insertion of a sequence, especially of sequences that regulate transcription, such as a promoter, or splice donor and acceptor sites often results in regulatory problems. Retroviruses utilise for all processes of transcription, RNA processing and translation several host cell mechanisms. Accordingly, various cis-acting sequences, either located in coding or in non-coding regions have been described for different retroviral genomes. These cis-acting sequences interact with various host cell proteins to regulate gene expression, RNA processing (15), polyadenylation (24), stability (46; 47), or nuclear export of viral RNA (48). Accordingly, it must be expected that the disruption of any such cis-acting elements severely impairs viral replication and productive generation of infectious viral particles, respectively. This is in line with a report by Yin & Hu who found that insertion of a translational cassette into the viral genome can severely influence or destroy viral propagation (45). Yin & Hu showed that the insertion of a cassette containing an IRES attached to a heterologous gene between the LTR and env-coding sequence of the viral body can—probably due to splicing interference (45)—destroy particle production of the used retroviral vector. Accordingly, this region or at least parts of this region are essential for viral replication and very sensitive to alterations.

Furthermore, complications of viral replication capacity, probably due to disrupted cis-acting sequences, aberrant transcripts or promoter interference, have been reported for recombinant retroviruses or retroviral vectors carrying an expression cassette with an SV40 promoter followed by dihydrofolate reductase gene (dhfr) (36, 37) in the 5'-end of the retroviral LTR.

Accordingly, all previously reported retroviral vectors carrying an IRES cassette have lost the ability to replicate in normal cells. Only Murakami et al. reported an avian retroviral vector construct comprising an IRES translational-cassette at a site at which the oncogene src has been deleted, which retained replication-competence for a few passages. However, said vector showed reduced expression levels of the heterologous gene (26). Since the virus used was an avian retrovirus it is not replication competent in mammalian cells.

As yet, it is not completely understood how cis-acting elements influence or control the viral life cycle. Nevertheless, it seems to be clear that disruption of cis-acting elements by randomly inserting a cassette into the genome of recombinant retroviruses results in promoter interference (9), disturbed splicing balance (46) or lack in packaging efficiency (8), and finally leads to the loss of viral replication or decreasing viral titers.

OBJECT OF THE INVENTION

It is an object of the present invention to improve recombinant retroviruses or retroviral vectors for gene transfer into target cells. Especially, it is an object of the present invention to insert a translational cassette into a retroviral genome without preventing viral replication and generation of viral particles, respectively.

DESCRIPTION OF THE INVENTION

To achieve the foregoing and other objects, the present invention provides a retroviral vector, comprising all of the retrovirus characteristic genes and, in addition, a heterologous internal ribosome entry site (IRES). In this application the term "maxi-virus" is used to refer to such replication-competent recombinant viruses for expression of heterologous genes. Hence, according to an embodiment of the present invention, the IRES is introduced into the retroviral vector without creating space for the insertion of the heterologous sequence into the vector by deleting complete viral genes. Although a heterologous sequence of certain length is additionally inserted into the retroviral genome the resulting construct can efficiently be replicated by the retroviral replication machinery. This surprising effect is also found even when in addition to the IRES, a further nucleotide sequence, especially one or more heterologous genes are inserted into the vector. Moreover, even if an additional IRES-cassette, comprising a further IRES plus a heterologous gene, is inserted into the vector, the resulting retrovirus remains replication competent.

According to the present invention the retroviral vector may comprise up to 7 kilo base pair (kbp) heterologous sequences, preferably up to 6 kbp, more preferably up to 5 kbp, more preferably up to 4 kbp and even more prefered up to 2 kbp heterologous sequences.

Furthermore, in case that an IRES-cassette, comprising one or more heterologous genes preceded by IRES is inserted into the vector, it was also demonstrated that after infection of a target cell with the retroviral vector and after integration of the proviral DNA into the genome of the target cell, the expression of the heterologous gene starting from the preceding IRES is not negatively influenced by internal interference or unbalanced RNA splicing activity. Furthermore, said expression takes place even if no cellular promoter transcribing a read-through RNA, which comprises both cellular DNA and proviral DNA, is active.

The term "characteristic genes" comprises all genes naturally occurring within the retroviral genome and comprises especially genes encoding virion proteins such as gag and pol, but also additional genes such as e.g. sag and src. However, the genes can also be replaced by homologous genes, i.e. by genes with 60 to 79%, preferably 80 to 89% and most preferably 90 to 99% nucleotide identity or by genes of closely related viruses. Parts of the nucleotide sequence of the characteristic genes may even be deleted without loss of the gene function.

The term "heterologous" is used hereinafter for any combination of nucleic acid sequences that is not normally found intimately associated in nature. The heterologous genes according to the present invention are preferably selected from, but not limited to the group of marker genes, therapeutic genes, such as anti-viral genes, anti-tumour genes, cytokine or chemokine genes, suicide genes, such as e.g. the cytosine deaminase gene of *Escherichia coli*, the thymidine kinase gene of herpes simplex virus type 1, or a mammalian cytochrome P450 gene (CYP2B1), or toxic genes, such as e.g. the pertussis toxin gene or tetanus toxin gene.

According to a preferred embodiment of the invention, IRES or the translational cassette with at least one heterologous gene preceded by IRES is inserted in the long terminal repeat (LTR) of the retroviral vector. Against common expectations, it was found that this insertion into the LTR does not destroy relevant cis-acting retroviral elements. This was particularly surprising, since it was not predictable that the retroviral LTR, which harbours most retroviral control elements, could be used as insertion site for a translation cassette. Quite to the contrary, it must have been expected that such insertion into the LTR would seriously hamper viral propagation or particle production due to the disruption of cis-acting sequences. However, the insertion of a translational cassette into the LTR according to the present invention did not inhibit viral replication or particle production.

According to a further preferred embodiment of the invention, IRES or the translational cassette with at least one heterologous gene preceeded by IRES is inserted outside the LTR, preferably between the end of the coding sequence of the env gene and the 5'end of the 3'LTR in a retrovirus. Most preferably the insertion is done in the polypurine tract upstream of the 3'LTR. If the retroviral vector should be a replication competent vector, the translational cassette should be inserted in a position of the genome where the insertion does not disturb the expression of any retroviral gene needed for replication.

The IRES element according to the present invention are selected from IRES isolated from picornaviridae, such as murine encephalomyocarditis virus (EMCV), poliovirus or foot and mouth disease virus (FMDV), retroviridae such as e.g. murine leukemia virus (MLV) or reticuloendotheliosis virus (REV), and/or retroposons such as e.g. VL30 (54; 55; 56; 57; 58). The term "IRES" in the context of the present invention also refers to any other RNA element capable of initiating non CAP dependant translation such as the 76 nt start sequence for initiating translation as described in (43)

The distance between the IRES element of EMCV and the start codon of the heterologous gene in a translational cassette is variable. However, best results were achieved when a distance similar to that as found in the wild-type virus genomes between IRES elements and the start codon of a wild-type gene is chosen. Furthermore, increased translation efficiency is obtained if at position −3 (3 nucleotides upstream the translation start codon) an adenine is located.

The normal retroviral vector comprises two complete LTRs—a 5' and 3' LTR—both comprising subregions, namely the U3-, R- and U5-region. The U3 region incorporates all regulatory elements and/or promoters, which are responsible for the transcription and translation of the retroviral genome. Additionally, at the 5' end of the U3-region the so-called inverted repeats (IR) are located. The IR are involved in the integration process of proviral DNA into the genome of a target cell. The R-region starts, per definition, with the transcription start codon and further comprises a polyadenylation signal. This polyadenylation signal, however, is only activated in the 3'LTR and thereby, marks the end point of a mature retroviral RNA transcript. It is assumed that, the U5 region of the LTR comprises one out of several packaging signals of the retroviral genome.

After integration of the retroviral vector into a cellular genome generation of retroviral particles occurs. For this, the integrated retroviral vector DNA must be transcribed into retroviral RNA. For generation of the retroviral RNA transcription starts at the transcription start site in the 5'R-region and stops at the polyadenylation site of the 3'R-region. Accordingly, the retroviral RNA genome comprises two incomplete LTRs. While the 5'LTR still comprises the R- and U5-region, the 3'LTR contains the U3- and R-region. After infection of a further target cell the retroviral genome has again to be integrated into a host cell genome. For this integration process, the retroviral RNA must at first reverse transcribed into DNA. During reverse transcription of the retroviral RNA genome into the so-called proviral DNA the 3'LTR U3-region is duplicated and shifted from the 3'LTR to the 5'LTR. Additionally, also the U5-region, which is only contained in the 5'LTR of the retroviral RNA genome, is duplicated and shifted during reverse transcription to the second LTR, namely the 3'LTR. Consequently, after reverse transcription the proviral DNA comprises again two complete LTRs.

Due to the above described retroviral replication particularity, especially to the duplication of the different regions of the retroviral LTR during the reverse transcription, different types of retroviral vectors are included in the present invention. One type of retroviral vectors according to the present invention can be regarded and is designated hereinafter as "short-term expression vector". In short-term expression vectors the translational cassette is inserted into the retroviral 5'U3-region and/or 3'U5-region. Such short-term expression vectors are particularly useful for the expression of heterologous genes in the packaging cell: After transfection of a packaging cell with short-term expression vector, said vector integrates into the genome of the packaging cell. Then the cellular transcription machinery transcribes the viral RNA genome, which will be packaged. Additionally, also the heterologous gene of the translational cassette is transcribed resulting in synthesis of the gene product of the heterologous gene in the packaging cell. Said gene product may support e.g. particle formation in the packaging cell or infectivity of the resulting particle. Additionally or alternatively, the gene product may simply be included into the viral particle, which is, correspondingly, used as vehicle for transfer of the gene product into the target cell. However, the retroviral RNA genome, which will be packaged into such particles, does not incorporate the heterologous gene, since the 5'U3-region and 3'U5-region are not incorporated in said viral RNA genome, but will be, as described above, newly generated by duplication during the following reverse transcription.

Another type of retroviral vectors according to the present invention is designated hereinafter as "long-term expression vector". For the construction of long-term expression vectors the translational cassette is inserted into the 5'U5-region and/or into the 3'U3-region of the retroviral LTR. Such long-term expression vectors are particularly useful to transfer heterologous genes via the retroviral vector genome into a target cell, since in these vector constructs the translational cassette comprising said heterologous genes remains integrated into the retroviral genome within the retroviral life cycle. The transferred genes are then integrated into the genome of the target cell and expressed for a long-term period.

In a preferred embodiment of the present invention the translational cassette is inserted into the U3-region of the 3'LTR preferably between the inverted repeats and the transcription-regulatory elements of the U3-region (FIG. 1). This insertion into the U3-region of the 3'LTR guarantees that after infection and during reverse transcription this U3-region including the inserted cassette is duplicated and shifted also to the 5'LTR. Thus, the resulting proviral DNA comprises said translational cassette in the U3-region of the LTRs on both ends.

Subsequently, this proviral DNA randomly integrates into the DNA genome of the infected cell. This process is mediated by the retroviral integrase. After successful integration the proviral DNA is transcribed by host cell mediated transcription into a new retroviral RNA genome. This transcription starts at the R-region of the 5'LTR, continuous alongside the viral body and finally stops at the polyadenylation signal at the R-region of the 3'LTR. Accordingly, the new retroviral RNA genome again comprises incomplete LTRs. Nevertheless, the resulting retroviral RNA genome contains at least two ORF. One ORF, which encodes genes of the viral body and the other ORF encoding the heterologous gene operably linked to the IRES inserted into the 3'U3 region. Accordingly, this resulting RNA molecule is a bi- or polycistronic RNA.

According to a further embodiment of the present invention the translational cassette is inserted into the R-region of the 5'LTR and/or 3'LTR of the retroviral vector. Insertion of the cassette in either one or both of these R-regions guarantees that the inserted cassette remains integrated into the retroviral genome during the retroviral life cycle. Integration into the R-region of both LTRs results in RNA transcripts comprising two copies of said cassette.

Two copies of the translational cassette are also obtained when the cassette is, e.g., integrated into the U3-region of the 3'LTR as well as into the U5-region of the 5'LTR. However, insertion into either the U3 or the U5 region leaves only one copy in the RNA genome where the IRES translational cassette is operational.

The use of RNA transcripts comprising two operational copies of the translational cassette (e.g. if inserted into the R-region) results in higher amounts of protein synthesis of the heterologous gene, which is encoded twice in the RNA molecule. Such increased amounts of protein synthesis are particularly useful for gene therapy and/or cancer treatment.

Independent of the localisation of the translational cassette into the retroviral LTR, the transcription of the retroviral genome is always controlled by the regulatory elements and/or promoter in the U3-region of the 5'LTR. According to a further embodiment of the present invention these regulatory elements and/or promoters can be replaced by other retroviral, viral or cellular regulatory elements and/or promoters. For this, the 3'U3-region of the retroviral vector is modified by partially deleting and/or replacing the original regulatory elements and/or promoter with the desired regulatory element and/or promoter. Preferably, such regulatory elements and/or promoters are selected from different viruses, such as e.g. cytomegalovirus (CMV), human immunodeficiency virus (HIV), Herpes simplex virus, or from cellular genes. Beside constitutive expressing promoters, cell specific or inducible promoters are used.

Such inducible or cell specific regulatory elements and/or promoters are preferably, but not limited to one or more elements of the group consisting of regulatory elements and/or promoters of the Whey Acidic Protein (WAP), Mouse Mammary Tumour Virus (MMTV), β-lactoglobulin or casein, which are used to target human mammary tumours; pancreas specific regulatory elements and promoters including carbonic anhydrase II or β-glucokinase regulatory elements and promoters; lymphocyte specific regulatory elements and promoters, immunoglobulin and lymphocyte specific regulatory elements and promoters; MMTV specific regulatory elements and promoters such as $^{MMTV}P2$ conferring responsiveness to glucocorticoid hormones or directing expression to the mammary gland, T-cell specific regulatory elements and promoters such as of the T-cell receptor gene and CD4 receptor promoter; or B-cell specific regulatory elements and promoters such as the immunoglobulin promoter or mb1.

The retroviral vector according to the present invention may be based on any retrovirus. Preferably, it is a non-avian, and most preferably, a vector based on Akv-murine leukemia virus (Akv-MLV). Akv-MLV shares, for example, 80% nucleic acid sequence homology and 90% homology at the protein level with Moloney murine leukemia virus (MoMLV). Additionally, Akv-MLV is highly homologous to SL-3-3-murine leukemia virus (SL3-3-MLV) with a nucleotide sequence of 98% homology. Accordingly, the present invention is particularly useful to develop further retroviral vectors based on MoMLV, SL-3-3-MLV or any further related virus, e.g. murine leukemia virus (MLV).

Additionally, SL3-3-MLV vectors are particularly useful for infection of lymphocytes. Accordingly, such SL-3-3-MLV vectors are preferably used to transfer therapeutic genes specifically to lymphocytes and thereby, specifically treat or prevent infectious diseases or proliferative disorders of the haematopoetic system. Most preferably, vectors based on VIRAGFPM and/or on AENGFMK2 (see table 1) are used.

According to still a further embodiment of the present invention the retroviral vector is constructed as a replication-defective vector based on any of the above-mentioned retroviruses (MOMLV, MLV, Akv-MLV, SL-3-3-MLV) or is, e.g., derived from the vectors of the ProCon family (for complete disclosure see also PCT/EP95/03445), of the pLXSN-(52) or pBag-family (53). In the context of the present application the term "mini-virus" is sometimes used to refer to such replication-defective recombinant viruses for the expression of heterologous genes. In case of a replication-defective retroviral vector, one or more genes essential for virus replication, packaging of viral RNA and/or infective particle formation, have been deleted from the retroviral vector. Thus, to reconstitute the viral life cycle and generate viral particles comprising such replication defective vectors a specialised producer cell providing the deleted genes is needed. Such producer cell are constructed by transducing a cell with DNA constructs encoding the genetic information of the retroviral proteins, which are essential for packaging a retroviral vector genome and generating viral particles. Notably, due to the transduction with the genetic information of the retroviral proteins a producer cell generates in the absence of a retroviral vector genome empty viral particles, which likewise will be released. In comparison to this, in the presence of a retroviral vector genome the producer cell will generate infectious viral particles, which comprise the retroviral vector genome. Such producer cells are also designated as packaging cells. The packaging cells according to the present invention are preferably, but not limiting, selected from a packaging cell lines e.g. selected of the group consisting of PA317 (49), BOSC23 (29), ψ or PG13 (50; 51) and/or any of these cell lines, additionally, transfected with further constructs allowing expression of surface proteins from other retroviruses. The replication-defective retroviral vector according to the present invention could also be termed as a "conditional replication-competent retroviral vector", since the vector replicates if the missing viral functions (e.g. gag/pol genes) are provided by the cells.

For the production of infectious retroviral particles, in general, a packaging cell culture, which, as described above, is already transfected with the genetic information and/or genes essential for retroviral particle formation, is super-transfected with the retroviral vector DNA. The term "super-transfection" describes—in the context of this specification—a "second" transfection event, namely the transfection of the packaging cell with the retroviral vector. The resulting supertransfected packaging cell will subsequently produce infectious viral particles comprising the retroviral vector RNA genome. Said particles, which will be released from the packaging cell, can be isolated. It should be noted that only supertransfected packaging cells produce infectious viral particles. Accordingly, the transduction efficiency directly correlates with the amount of infectious viral particles produced.

This already indicates that one disadvantage of the described process of retroviral particle production within a packaging cell culture is a limiting transduction efficiency of the packaging cells.

A further disadvantage of a normal packaging cell culture is the resistance of the packaging cells against infection with viral particles, which e.g. have been freshly produced in the packaging cell culture. This resistance is mediated by the expression of the retroviral Env-protein in the packaging cell. The Env-protein is capable to bind to cell membrane receptors. These cell membrane receptors are involved in the attachment of infectious viral particles onto a cell and thus, in the infection of the cells with viral particles. Accordingly, no further attachment of viral particles is possible to a packaging cell, wherein the cell membrane receptors are bound to the intracellularly produced retroviral Env protein. Thus, said packaging cell is resistant to any further infection or so-called superinfection, respectively. The term "superinfection" describes—in the context of this specification— any infection event with a viral particle upon an already transduced packaging cell. Accordingly, in a normal packaging cell culture no further transfer of the retroviral vector genome to a further packaging cell is possible. Thus, no increase of the transduction efficiency and, accordingly, of the viral particle production can be obtained.

Therefore, the present invention also provides in a further embodiment a retroviral vector, which is useful to increase the transduction efficiency and, likewise, to increase the viral particle production in a packaging cell culture.

According to this embodiment of the invention, a replication-defective retroviral vector is provided, said vector comprising a gene encoding a protein which is capable to initiate infection, wherein said gene is under translational control of a heterologous IRES. Since the retroviral vector according to the present invention encodes itself env, a packaging cell needs only to provide the proteins encoded by gag and/or pol. Such packaging cells comprising a gag and/or pol encoding DNA construct, but no env encoding DNA construct is called semi-packaging cell. Advantageously, this semi-packaging cell is not resistant to superinfection since these cells do not express Env protein prior to transfection with the retroviral particle. Consequently, no Env protein binds to the cellular receptor and thus, no resistance is mediate in said cell. Accordingly, only after transfection of the packaging cell with the retroviral vector viral particles are generated and released. These retroviral particles comprising now a functional env gene, can and will infect further semi-packaging cells in culture. Thus, the retroviral vector according to this embodiment is replication-competent in the semi-packaging cells and thus allow an easy and highly efficient production of the retroviral particles in high titers. Furthermore, the retroviral vector has the advantage that, as soon as infectious particles produced in these semi-packaging cells infect target cells that lack gag and/or pol, only the genetic information of the retroviral vector is transferred. Since this vector according to this embodiment does not comprise the gag and/or pol, no further replication of the retroviral vector in the target cell is observed. Accordingly, said replication-defective vector is a safe vector e.g. for use in gene therapy.

The term "protein which is capable to initiate infection" comprises all proteins which allow a retrovirus to adhere to the membrane of a host cell and/or to enter into the host cell. Said proteins may be viral surface proteins, preferably an Env protein or functional derivatives thereof. The env gene may originate from the same retrovirus on which the retroviral vector according to the present invention is based. However, preferably, the env gene is heterologous to the retroviral vector and most preferably it is derived from different viral species, subspecies, subtypes or clades. Furthermore, the protein, which initiates infection may only be a part of a naturally occurring protein or may be only 60–69%, preferably 70–89%, and most preferably 90–99% identical to the amino acid sequence of the naturally occurring protein. All of the above mentioned variants of the protein which initiates infection are in the following called "env".

The retroviral vector according to the present invention may comprise in addition to the IRES cassette comprising the IRES with the env gene one or more further genes. In a preferred embodiment, the vector comprises in addition to the IRES-env-cassette gag or pol, wherein most preferably, gag or pol is preceded by an additional IRES.

In another preferred embodiment, said vector comprises in addition to the IRES-env-cassette one or more heterologous genes, most preferably inserted 5-prime of the IRES-env cassette. Advantageously, in contrast to naturally occurring retroviruses, the heterologous gene(s) and env are translated from the same full length mRNA. Since splicing is not required the heterologous gene is expressed over a long period of time, and deletion of the heterologous gene is prevented. Accordingly, the vector according to the present invention is advantageous compared to the previously known vectors, in which env was expressed from a spliced mRNA. For example, Nouvel et al. 1994 (Virology 204: 180–89) made a retroviral vector in which a heterologous gene and env was translated from the subgenomic spliced mRNA of exactly the same structure as the env mRNA made in normal replicating virus. However, this vector was rapidly overgrown by vectors having deleted the heterologous gene.

According to a further embodiment of the invention a method for the selection of vectors with new properties, such as the ability to infect a specific cell type, is provided. According to this embodiment of the invention, a vector library comprising a complex mixture of the replication-defective vector according to the present invention with variants of the env gene is produced. Such a library can be made e.g. by introducing random mutations into a selected part of the env gene or by introducing random cDNA fragments into the env gene. Instead of being inserted directly into the envelope gene, the random sequences can also be presented by a heterologous protein, which serves as a scaffold, e.g. the random sequence may be inserted into a single chain antibody gene embedded in the envelope gene. After producing said vector library, cells of a specific cell type are transfected with the vectors of said library. Subsequently, the cells are incubated under conditions, which allow the amplification of the retroviral vector. Accordingly, viral particles are produced, wherein each particle has one variant of env. Since env determines the infection characteristic of a retroviral particle, the produced retroviral particles have different infection characteristics. Some of the produced viral particles are more infectious for this specific cell type than others. Some of the viral particle will even not be able to form viral particles and/or to infect cells at all. Hence, when the produced viral particles infect further, not yet infected cells, some viral particles with a specific variant of env will be more successful, resulting in the enrichment of said viral particles. Hence, the viral particle, which is most successful in infecting this specific target cell and/or in the amplification in said target cell will be most abundant. The vectors are then recovered, characterized and used for additional studies. For example, the gene coding for an altered envelope protein selected according to this embodiment of the invention could be used to make a packaging cell with the purpose to produce virus particles that infect only specific cell types.

According to a preferred embodiment, this selection method is applied for the selection of a heterologous envelope protein, which is suitable to function in the environment of a virus of e.g. other species, subtypes or clades. When a heterologous envelope protein is inserted into the minivirus (i.e. a virus that is not replication competent), the resulting virus is often poorly infectious, since the components of the different viruses are not adapted to function together. However, mutations in the envelope protein or in genes of the minivirus may improve the function in this heterologous context. Hence, some vectors may work better than others when they are mutated in the proper region. If these miniviruses with different envelope proteins are, e.g., replicated on a semi-packaging cell line those that are most infectious will be most abundant and can be selected for further analysis and use.

After introducing a replication-competent, semi-replication-competent or a replication-defective retroviral vector, according to the present invention, into a target cell or a producer cell line, respectively, retroviral particles comprising the recombinant retroviral genome are generated and subsequently released from the transduced cell. Accordingly, the present invention also provides host cells, producer cells and retroviral particles comprising the retroviral vector of the present invention.

The invention further includes a retroviral provirus, mRNA of a retroviral provirus according to the invention or any RNA transcribed from a retroviral vector according to the invention. Furthermore, the invention includes host cells transduced or infected with a retroviral particle.

According to the present invention the retroviral vector as well as RNA thereof, the producer or host cell, and/or the retroviral particle are used for gene therapy in mammals, including humans, or for the production of a pharmaceutical composition for in vivo and in vitro gene therapy.

Still a further embodiment of the invention provides a method for introducing homologous and/or heterologous nucleotide sequences into target cells comprising transducing a target cell population in vivo or in vitro with the retroviral vector according to the invention or the recombinant retroviral particles according to the invention.

This method is particularly of interest for the production of transgenic animals. For starting a transgenic animal line, firstly so-called founder animals, which comprise the relevant transgene in their germ line cells, must be established. Such founder animals, which are in their germ line cells heterozygous for the transgene, are then used to produce descendants. The term "heterozygous" indicates that the transgene is found on one copy of a chromosome of a diploid cellular genome. In comparison with that the term "homozygous" indicates that both copies of the chromosomes of a diploid genome comprise the transgene. As the result of breeding with the founder animals one out of four offspring will be homozygotic for the transgene according to the Mendelian law of hereditism. Furthermore, the result of breeding with such homozygous transgenic animals is a transgenic animal line, comprising in all cells of their body the transgene.

The main problem regarding the generation of transgenic animals is to obtain sufficient transduction efficiency in the germ line of a founder animal. Normally, embryonic stem cells, which can be introduced into early embryos, are manipulated in vitro, selected for transgenic activity and subsequently re-introduced to the early embryos. Since such embryonic stem cells have still a pluripotent potential, some of them will differentiate also to germ line cells. This method has a low efficacy and is very time consuming.

According to the method of the present invention, embryonic stem cells or early embryos, respectively, are infected either in vitro or intra utero with the retroviral particle according to the present invention. After infection the retroviral vector integrates into the genome of the embryonic cell. Once the retroviral vector is integrated into the genome of an embryonic stem cell it will be transmitted by regular cell division into all descending cells. Since optionally the retroviral vector used is replication-competent said vector also produces further infectious retroviral particles in the infected embryonic cell. These particles infect further embryonic cells and thus, potentially increase the probability to obtain germ line transduction. Accordingly, the method according to the present invention is highly efficient to obtain germ line transduction. Since the efficiency of the germ line transduction corresponds to the success to finally obtain transgenic animals, the method according the present invention provides a fast and efficient technology to produce transgenic animals. This method is applicable to mammals, but also to other genera such as birds or fishes. This will of course not work with mice and the normal battery of retroviruses and derived vectors as these instantly becomes inactivated in cells of the germ line such as ES or EC cells.

Since about more than 90% of the mammalian genome consists of non-coding regions, retroviral induced germ line transduction leads normally to insertion of the vector into non-coding regions. Thus, a transgenic cell comprising the integrated vector normally expresses at least one additional gene as encoded on the retroviral vector. Such additional gene, which is translated from the integrated retroviral vector according to the present invention, essentially simplifies the detection of transduced cells, but also of potential founder animals. Insertion of the vector may also occur into a coding region of the cellular genome. This way of retroviral transduction usually leads to the destruction of said cellular coding region. Accordingly, this strategy is particularly interesting for the generation of so-called knockout animals.

According to a further embodiment the method of the present invention for introducing heterologous nucleotide sequences into target cells of animals can be used for the determination of gene function by insertional activation, insertional inactivation or insertional mutagenesis of host genes. The heterologous gene can be e.g. an oncogene, a dominant negative version of a tumor suppressor gene or any other sequence that may interfere with oncogenesis, preferably with oncogenesis induced by viruses. According to this embodiment the animal is preferably a mouse. The retroviral vector is preferably injected into newborn animals.

SUMMARY OF THE INVENTION

The invention comprises, inter alia, the following, alone or in combination:

A retroviral vector comprising all for the retrovirus characteristic genes, wherein all genes essential for replication of the retrovirus remain functional, said vector additionally comprising a heterologous internal ribosome entry site (IRES).

The retroviral vector as above comprising a heterologous gene preceded by the IRES, resulting in the translation of said heterologous gene under the control of the IRES.

A replication-defective retroviral vector comprising a gene encoding a protein which is capable to initiate infection, wherein said gene is under translational control of a heterologous internal ribosome entry site (IRES).

The retroviral vector as above, wherein the IRES or the translational cassette with at least one heterologous gene preceeded by IRES is inserted between the end of the coding sequence of the env gene and the 5'end of the 3'LTR in a retrovirus.

The retroviral vector as above, wherein the IRES or the translational cassette with at least one heterologous gene preceeded by IRES is inserted in the polypurine tract of a retrovirus upstream of the 3'LTR.

The retroviral vector as above, wherein the gene encoding the protein which is capable to initiate infection is an env gene or a functional derivative thereof.

The retroviral vector as above comprising a heterologous env gene.

The retroviral vector as above, wherein env and the retroviral vector are derived from different species, subspecies, subtypes or clades.

The retroviral vector as above, wherein gag is additionally included in the vector.

The retroviral vector as above, wherein pol is additionally included in the vector.

The retroviral vector as above, wherein gag or pol are preceded by an additional IRES or by a promoter and/or enhancer element.

The retroviral vector as above, comprising an additional heterologous gene.

The retroviral vector as above, wherein said additional heterologous gene is expressed under the control of an additional IRES or by a promoter and/or enhancer element.

The retroviral vector as above, wherein the IRES is inserted into the Long Terminal Repeat (LTR).

The retroviral vector as above, wherein the IRES is inserted in the U3 region of the LTR.

The retroviral vector as above, wherein the IRES is inserted in the U3-region of the 3'LTR.

The retroviral vector as above, wherein the IRES is inserted in the U3 region between the inverted repeats and the transcription-regulatory elements.

The retroviral vector as above, wherein the used IRES is selected from the IRES elements of picornaviridae, retroviridae or retroposons.

The retroviral vector as above, wherein the retroviral vector is based on a murine leukemia virus (MLV), Moloney murine leukemia virus (MoMLV), Akv-MLV, SL-3-3-MLV or other closely related virus.

An RNA of the retroviral vector as above.

A retroviral provirus produced in a target cell during the process of reverse transcription of the RNA as above.

An mRNA of the retroviral provirus as above.

A retroviral particle comprising the RNA as above.

A retroviral particle as above obtainable by transfecting a packaging cell with the retroviral vector described above or the RNA described above.

A producer cell comprising a retroviral vector as above.

A host cell comprising a retroviral vector as above.

A host cell infected with a retroviral particle as above.

The retroviral vector as above, the producer cell as described above, the retroviral particle as described above and/or the host cell as described above for use in gene therapy.

Use of the retroviral vector as described above, the producer cell as described above, the retroviral particle as described above and/or the host cell as described above for producing a medicament for gene therapy.

A pharmaceutical composition containing a therapeutically effective amount of the retroviral vector as described above, the retroviral as described above, the producer cell as described above, and/or the host cell as described above.

A method for introducing homologous and/or heterologous nucleotide sequences into target cells comprising infection of a target cells with retroviral particles as described above.

The method as above for the production of transgenic animals comprising infection or transduction of embryonic cells with the retroviral particles as above or the retroviral vector as above.

A method for selection of viral particles comprising a retroviral vector as described above for specific infection of a specific target cell, wherein cells of a packaging cell line are infected with a vector library comprising said retroviral vectors including variants of the gene encoding the protein which is capable to initiate infection and wherein said infected cells are incubated under conditions which allow amplification of said retroviral vectors, resulting in viral particles each comprising one variant of the protein which is capable to initiate infection and wherein further not yet infected cells are infected by said viral particles resulting in enrichment of viral particles comprising one of the protein variants, said viral particles being highly adapted to infect said target cell.

The method as above, wherein said gene encoding the protein which is capable to initiate infection is an env gene.

The method as above, wherein said gene is a heterologous env gene.

FIGURE LEGENDS

FIG. 1: A) Proviral structure, RNA transcripts and proteins of AkvBi-EGFP (in AkvBi-neo the EGFP-gene is substituted by the neomycin phosphotransferase II gene). gag, pol, env: retroviral genes; EGFP: gene encoding the green fluorescent protein, codon usage optimized for eukaryotic cells; IRES: internal ribosome binding site from EMCV; stippled line, intron; U3, R, U5: LTR elements; PPT: polypurine tract; IR: inverted repeat; CelII: restriction sites used for insertion of the IRES-EGFP cassette; arrows in the U3: 99 bp repeats which are major determinants for the enhancer function (21); Q: packaging signal; SD: splice donor site; SA: splice acceptor site; p(A): polyadenylation signal; AAAAA: polyA tail B) General proviral structure of constructs according to the present invention. The translational cassette (here specified as an IRES-EGFP cassette) can be inserted into the U3 region of the 3'LTR (above) or into the PPT region between the end of the env gene and the 5'end of the 3'LTR (below). PBS: primer binding site; PSI: packaging signal; all other abbreviations as in FIG. 1A). (see also table 1)

FIG. 2: Leader sequences from the termination of the IRES to the start codon of the operably linked genes FIG. 3: Proviral structure and transduction efficiency of Akv wild type and derivatives thereof. An IRES-neo or IRES-EGFP sequence was inserted at the Cel II site of the U3 region in the 3'0 viral LTR to generate pAkvBi-neo and pAkvBi-EGFP, respectively. λ DNA fragments were inserted at the Not I sites and Xho I sites to generate Mega-vectors and Mega-pol-vectors. The sizes of the full-length RNAs are indicated in nucleotides (nt). Titer (CFU/ml) G418 column shows numbers of neomycin (neo)-resistant NIH 3T3 colonies after one round of transfection for each construct. Titer (CFU/ml) G418+Mab is the same experiment as before, with the exception that an envelope neutralizing antibody 83A25 was added to the culture for preventing secondary infection events during the selection procedure (Evans et al., *J. Virol* 1990; 64:6176–83). A digestion with Afl II was made to delete 1.5 kb and BstE II, to delete 3.5 kb from the vector, giving a deletion of aproximately 5000 nt in the RNA genome and bringing the RNA genome size from 14.000 nt to aproximately 9000 nt, Mega-4 kb-AflII-BstEII. Arrows in the construct are placed at the beginnig and end of the genes to mark the deletions. The Figure above shows the plasmids used in the transfection experiment and number of neomycin (neo)-resistant NIH 3T3 colonies after one round of transfection. CFU: Colony forming units; bp: base pairs; nt: nucleotides. Dark grey boxes: LTR elements; light grey boxes: internal ribosome entry site (IRES) from EMCV preceding the neomycin resistence gene (neo) or the gene encoding the green fluorescent protein (EGFP); zeo: zeocin resistance gene; λ: lambda-DNA; gag, pol, env: retroviral genes.

EXAMPLES

The following examples will further illustrate the present invention. It will be well understood by a person skilled in the art that the provided examples in no way may be interpreted in a way that limits the applicability of the technology provided by the present invention to this examples.

Example 1

Construction of Replication-Competent Retroviral Vectors Containing an IRES Cassette in the LTR To examine the possibility of constructing replication-competent murine leukemia viruses, which express heterologous genes, an EMCV IRES-neo cassette (18) was inserted into the CelII site in the 3'LTR of SL3-3-MLV and Akv-MLV (FIG. 1). Thus, the IRES-neo cassette from pJD214HyBi+ (17)(from coordinate 270 in the EMCV map (12) to stop codon neo) was amplified by polymerase chain reaction (PCR) (1398 bp)
5' primer: CAAGCTTAGCGGCCGCCCCCTAACGT-TACTG, (SEQID No: 1),
3' primer: TATGCTAAGCTCGACTCAGAA-GAACTCGTCAAG, (SEQID No: 2).

The leader sequence from the EMCV start codon 10, position 826 in the EMCV map, to the ATG start codon in neo is;
ATTGCCGCGTGTGGCCTCGAACAC-CGAGCGACCCTGCAGCCAATATG, (SEQID No: 3).

Additionally, for the construction of a retroviral vector containing an IRES-EGFP (green fluorescence protein) cassette, such an IRES-EGFP cassette was PCR amplified from a plasmid designated CMVbipe2-EGFP. This plasmid is based on the plasmid pJD214HyBi+ (17) and comprises instead of the neo gene the EGFP gene sequence (ClonTech, Palo Alto, USA). For the PCR amplification the following primers were used:
5' primer: GATCGCTTAGCTGCAGATGCATGGC-CCATGCGGCCGCCCCCT, (SEQID No: 4),
3'primer: (SEQID No: 5) ATGACTGCAGGCTAAGC-CATATGACGCGTACGGCCGCTTTACTTGACAGC.

The leader sequence from the EMCV start codon 10 to the ATG start codon in EGFP is; ATTGCCGCGTGTGGCCTC-GAACACCGAGCGACCCTGCAGCCGCG-GTCGACATG, (SEQID No: 6). Starting from these features several further vectors have been constructed, which only differ in the leader sequence from the EMCV start codon 10 to the ATG start codon of the EGFP gene. The relevant leader sequences are indicated in FIG. 2.

The IRES containing translational cassettes were inserted into the 3' LTR CelII site of plasmids pAkv (pAKV-59 (21, 22) with LTR regions and linkers from pPBS-Pro (25)) and pSL3-3 (a genomic clone of SL3-3 flanked by endogenous sequences inserted in the EcoRI site in pBR327 (GenBank Accession no: J02549), respectively, giving rise to pAkvBi-neo, pAkvBi-EGFP and pSL3-3Bi-neo. The chosen insertion site, at the CelII site, was located 27 bases from the 5'-end of the LTR. The inverted repeat, participating in the integration process, are not effected by the insertion and neither is the enhancer region of U3, as the major determinant for transcriptional regulation. Notably, the 99 bp repeats (20, 22) begins 110 bp downstream of the insert. According to the vector design the translation cassette, e.g. IRES-neo (FIG. 1) is predicted to be present in both unspliced (genomic) and spliced mRNA.

Additionally, the same IRES-neo cassette (17) was used for constructing the bi-cistronic zeo and neo expressing vector (neo stands for Neomycin resistance gene), designated pBi-zeo-neo. For this, the IRES-neo cassette was inserted in a zeo (Zeocin-gene) containing Akv-MLV based vector (MSS5, constructed by M. S. Sorensen from the monocistronic plasmid ptvAkv-neo (28)), giving rise to the bi-cistronic vector pBi-zeo-neo. This vector was expected, and proofed to give rise to an unspliced RNA transcript with zeo translated from the 5'-end and with a translation of neo by internal initiation, due to the enclosure of the EMCV-IRES element. Additionally, in the vector pBi-neo-zeo the IRES element was kept in place but neo and zeo were exchanged.

Generation of Viral Particles

For generation of recombinant viruses and virus production the constructs as above were transfected to the following cell lines:

The murine fibroblast cell line NIH3T3 was grown in Dulbecco's modified Eagle's medium containing 10% (vol/vol) newborn calf serum. Selection for neo resistant NIH3T3 cells was performed with 600 µg/ml G418 (active concentration, Calbiochem).

BOSC23 cells are derived from the Ad5 transformed human embryonic kidney 293 cell line (29). The BOSC23 cells were selected for guanine phosphoribosyltransferase (gpt) resistance with 25 µg/ml mycophenolic acid (Gibco), 20 µg/ml aminopterin (Sigma), 250 µg/ml xanthine (Sigma) and 60 µg/ml thymidine (Sigma) in Dulbecco's modified Eagle's medium containing 10% (vol/vol) fetal calf serum, but otherwise grown under the same conditions as NIH3T3.

All transfections were done by the calcium phosphate precipitation method (11). Fresh medium was supplied to confluent virus producing cells 24 hours before harvesting, except for the 24 h-BOSC23-experiment (see the following table "Transduction efficiencies", column 2 (24 h)) where fresh medium was added 8 hours before harvesting. Harvested viral supernatants were filtered through 0.45-µm-pore-size filters and added, by 10-fold end-point-dilutions, to six-well-dishes ($10^5$ NIH3T3 cells/12 cm² well) with 6 µg/ml polybrene. G418 was added 24 hours after transduction and selection continued for 12–14 days.

| | Transduction efficiencies | | |
|---|---|---|---|
| | Titer (G418 resistant colonies/ml) | | |
| Vector[a] | 24 h[b] | 72 h[b] | 72 h[c] |
| tvAkv-neo | $3 \times 10^4$ | $3 \times 10^5$ | — |
| SL3-3Bi-neo | $1 \times 10^4$ | $1 \times 10^5$ | $5 \times 10^5$ |
| Bi-zeo-neo | — | — | $4 \times 10^5$ |
| Bi-neo-zeo | — | — | $1 \times 10^6$ |
| AkvBi-neo | — | — | $5 \times 10^5$ |

[a]BOSC23 packaging cells were transfected with equal molar amount of vector constructs, BlueScript carrier was supplied up to a total of 15 µg DNA/80 cm² dish. Virus particles were harvested after 24 and 72 hours and transferred to NIH3T3 cells by end-point-dilutions.
[b] and [c] are different experiments.

Transduction Efficiency of Neo Expressing Maxi-Viruses

In the following we use the term maxi-viruses to indicate replication-competent recombinant viruses for expression of heterologous genes. Transduction experiments were performed in order to analyse if the neo expressing maxi-viruses, SL3-3Bi-neo and AkvBi-neo, could be transduced as efficiently from a transient transfected packaging cell line (BOSC23) as conventional retroviral vectors (see above table "Transduction efficiencies"). The neo expressing tvAkv-neo (28), Bi-zeo-neo, Bi-neo-zeo vectors were used as control.

The titers show that the maxi-viruses are transduced as efficiently as ordinary single-cistronic and bi-cistronic vectors by a titer of $5 \times 10^5$ neo resistant colonies/ml. Hence, the maxi-viruses are not inhibited in the transduction processes (transcription, packaging, reverse transcription, integration) when the IRES-neo cassette is inserted in the 5'-end of the LTR. Furthermore, these results show that the IRES-neo insert is functional in this viral context. For the vectors with neo located upstream (ptvAkv, Bi-neo-zeo) there seems to be a slightly higher transduction efficiency than for the vectors using internal initiation (Bi-zeo-neo, SL3-3Bi-neo, AkvBi-neo). This could be due to a reduced internal translation efficiency of genes supported by an IRES element, compared to genes located in an upstream position, as we and others (3, 17, 31) have observed for several IRES translation-supporting constructs. Lack of apparent reduction in the transduction efficiencies of AkvBi-neo and SL3-3Bi-neo, even though the RNA genome sizes are increased 1.4 kb, correlates with previous observations in MLV (6, 36).

Viral supernatants were harvested from ptvAkv-neo and SL3-3Bi-neo transfected packaging cells shortly (24 hours) after transfection in order to analyse a potential bias in the titers caused by maxi-viral produced proteins. The titers after 24 hours reveal the same difference between the conventional vector and the replication-competent vector as after 72 hours. Therefore, the production of viral proteins from SL3-3Bi-neo in the packaging cells does not seem to influence the viral titer.

During retroviral replication the U3 region of the genomic RNA is copied to the 5'end of the proviral DNA. By PCR analysis on genomic DNA from infected cells the heterologous insert in maxi-viruses was also found to be copied during replication to the 5' end of the provirus. Conceivably, for most proviruses only the 3' heterologous insert will be utilised for gene expression as there is no transcriptional start upstream of the 5' insert, but in cases where cellular transcripts proceed into the proviruses which have integrated in transcriptionally active genes, translation from the 5' heterologous gene would also be expected to occur. To examine this, the total RNA was extracted from cells by the acid guanidium thiocyanate-phenol-chloroform method (4) and Northern blot analysis was done by standard procedures (33) on a 1% agarose gel. Surprisingly, when analysing RNA from G418 selected maxi-virus infected cells by Northern blots with a neo-probe; no aberrant RNA's can be detected. This result together with the high transduction efficiency of maxi-viruses indicates that maxi-proviruses are not dependent upon host-DNA read-through transcripts for expression of the heterologous gene.

Replication Efficiency of Maxi-Viruses

To enable a more direct examination of viral spread in cell cultures or in animals an EGFP expressing maxi-virus, AkvBi-EGFP, was generated, as described above and included in parallel with the AkvBi-neo and SL3-3Bi-neo maxi-viruses in the following experiments. For analysis of the replication and infection efficiencies of the three maxi-viruses NIH3T3 cells transduced with a viral stock generated in BOSC23 packaging cells were used as virus producing cells. In all experiments with NIH3T3 cells as virus producer cells, populations of at least 1000 transduction events were used. The virus producer cells were either selected 14 days with G418 (AkvBi-neo, SL3-3Bi-neo) or grown for 7 days (AkvBi-EGFP) prior to measurement. For the AkvBi-EGFP infection experiment 10 ml of supernatant was harvested from a confluent 7-days AkvBi-EGFP infected culture (80 cm$^2$ dish), filtered and added to $8 \times 10^5$ NIH3T3 cells/80 cm$^2$ with 6 µg/ml polybrene. After the first day of infection the AkvBi-EGFP infected cultures were supplied with 1 µg/ml polybrene.

The titers obtained from these infected NIH3T3 populations were $10^3$ infectious units/ml (IU/ml) for SL3-3Bi-neo while it was about a thousand fold higher for AkvBi-neo. These findings have been especially surprising, since good expression of envelope protein from replication-competent recombinant retroviral vectors has not been observed before in mammalian cells.

| Infection efficiencies | |
|---|---|
| Maxi-virus[a] | Titer (IU/ml) |
| SL3-3Bi-neo[b] | $1 \times 10^3$ |
| AkvBi-neo[b] | $1 \times 10^6$ |
| AkvBi-EGFP[c] | $10^4$–$10^5$ |

[a] Virus particles harvested from confluent cultures of maxi-virus infected NIH3T3 cells were transferred to NIH3T3 cells by end-point dilutions.
[b] Producer cells were selected 14 days prior to titer experiment.
[c] A more than 95% positive population of AkvBi-EGFP infected cells were used as producer culture. After 7 days EGFP expressing cells were detected in the well corresponding to $10^4$–$10^5$ infectious unit.

For AkvBi-EGFP the titer was measured by flow cytometry analysis. For flow cytometry analysis cells were harvested and washed twice in PBS containing 2% fetal calf serum and 2 mM NaN$_3$. Cells were resuspended in the same buffer containing 1% formalin, and analysed on a Coulter® EPICS XL-MCL cytometer. More than 50,000 counts were analysed from each sample. Listmode analysis was performed using CellQuest® software from Becton Dickinson.

The measured titer for AkvBi-EGFP was up to $10^{4-10.5}$ IU/ml. A reduced titer was expected for AkvBi-EGFP compared the above titer experiment, as there is a high threshold level for detection of EGFP expressing cells (compare with Table above).

Altered levels of spliced RNA in maxi-viruses due to insertion of an IRES cassette. To analyse spliced RNA of the retroviral constructs the total RNA was extracted from maxi-virus infected NIH3T3 cells and Northern blot analysis, with the SmaI 330-bp envelope fragment of Akv-MLV (38) as hybridisation probe, was performed, as described above. For the maxi-viruses two major RNA transcripts were expected, an unspliced and a spliced mRNA, as observed in wt MLV's. Wt Akv has a balanced splicing of the two mRNA species with a spliced/unspliced ratio of 0.8 (quantified on a PhosphorImager®) while wt SL3-3 has a lower amount of spliced than unspliced RNA with a ratio of 0.4. For maxi-viruses, which have a lower mobility due to the heterologous inserts, the presence of IRES-neo or IRES-EGFP cassettes reduces the level of spliced RNA, to a spliced/unspliced ratio of 0.2 in Akv-maxi-viruses while no ratio can be stated for SL3-3Bi-neo as the amount of spliced RNA is below the detection limit of around 0.05. When looking at the exposure, bands corresponding to the spliced mRNA's can be recognised for AkvBi-neo and AkvBi-EGFP, while the spliced SL3-3Bi-neo band is absent and does not even appear on a longer exposure.

In order to investigate if the altered splicing leads to lack of envelope proteins for efficient replication pSL3-3Bi-neo together with an env expressing plasmid were transiently transfected into NIH3T3 cells and virus production was measured in a titer experiment. The transiently expressed envelope proteins improved the transduction efficiency of SL3-3Bi-neo about 35 fold compared to the control without env expression, suggesting the low replication efficiency of SL3-3Bi-neo to be caused by low splicing efficiency and thereby low production of envelope proteins. For the Akv-maxi-viruses the amount of spliced RNA is reduced but apparently not to a level where replication efficiency is drastically effected.

Genomic Integrity of AkvBi-EGFP During Multiple Infection Rounds

Genetic stability analysis was carried out by supplying virus supernatant from transfected BOSC23 packaging cells in the first passage and from infected NIH3T3 cultures in the succeeding passages to uninfected NIH3T3 cultures, resulting in passage one to six. The AkvBi-EGFP virus infected cells were cultured for seven days and supernatant was then transferred to uninfected cells. In the first passage, where supernatant was transferred from BOSC23 packaging cells 60–70% of the NIH3T3 cells were scored positive by microscopy after 2 days. For this, the cells were seeded in glass chambers (Nunc) and analysed by fluorescence microscopy.

Immediately prior to microscopy cells were washed in phosphate buffered saline (PBS) and PBS was added. Cells were visualised (200 times magnification) with an Olympus fluorescence microscope equipped with Olympus HQ:F801 fluorescence filter. This percentage of 60–70% of the EGFP expressing NIH3T3 cells in passage 1 gradually increased until day 5 where 95–100% of the cells were scored positive. For passage 2 to passage 5, 40–50% positive cells were detected after 2 days and an optimal expression percentage of 80–90% was reached at day 6. For passage 6, 20–30% EGFP-expressing cells were observed at day 2 and an optimal level at 50% was reached at day 6. Based on these observations we estimate that between one and three replication cycles, with an average of two replication cycles, are performed in each passage.

As judged by Northern blotting, the majority of AkvBi-EGFP viruses were genetically stable over several rounds of replication. For this, Northern blot analysis (as described above) of the six passages using a viral envelope were performed. RNA was extracted from the cells in the end of each passage, 7 days after infection. For the first two passages the Northern blot reveals only full-size viral genomes, while in the third passage deletion mutants appear with faint bands. The fraction of deletion mutants compared to wt AkvBi-EGFP increases during passage four and five and becomes the dominant viral population in passage six. These mutants have major deletions in the IRES-EGFP sequence, and have regained a balanced splicing. Whether the evolutionary driving force for the overgrowing of deletion mutants is the lack of a balanced splicing or of other factors involved in the replication of AkvBi-EGFP cannot be concluded from our experiments.

Interestingly, the two closely related viruses Akv and SL3-3 seem to differ in splicing regulation contributing to the low replication efficiency of the SL3-3Bi-neo vector. It is unlikely that this is caused by a mutation in the particular construct used since the deletion variants that appear upon cultivation replicate as efficiently as the SL3-3 wt virus. The splice donor and the splice acceptor site sequences in Akv and SL3-3 are very similar, only diverging by one less pyrimidine in the Akv 3' splice acceptor site polypyrimidine tract, indicating other cis-elements within the viral genomes to be responsible for the observed difference in splicing efficiency.

Flow cytometric analysis performed on the AkvBi-EGFP infected NIH3T3 cells (passage 1, 5, 6 and the NIH3T3 control) confirmed genomic integrity over several rounds of replication. From the flow cytometric profiles of the passages it is deduced that passage 1 has only a minor overlapping area with the NIH3T3 uninfected control, indicating that practically all cells in this population express EGFP above background. Passage 2 to passage 5 has almost identical flow cytometric profiles, where a major part of the cells express EGFP above the background levels. For passage 6 around half of the cells express EGFP correlating with the data of the Northern Blot analysis where the deleted AkvBi-EGFP-viruses become more and more abundant during the passages and finally become dominant in passage 6.

By using techniques similar to those described above numerous other recombinant maxiviruses were constructed and tested in which the heterologous gene was preceded by an IRES element:

a maxivirus based on Akv that expresses the Herpes simplex virus thymidine kinase gene from the U3 insertion site. This maxivirus has been tested positive for infection capability of NIH cells as well as gancyclovir mediated killing of AkvU3-HSV-tk infected cells.

a maxivirus comprising the viral oncogene H-ras a maxivirus comprising the bacteriophage P1 derived recombinase Cre that is an important tool for biotechnology Example 2

Construction of Retroviral Vectors Additionally Containing an IRES-env Translational Cassette To achieve replication within a packaging cell culture resistance against superinfection has to be avoided. This resistance is mediated by the Env-protein binding to the cell membrane receptor, thereby preventing attachment of viral particles (7). The new vector system circumvents this resistance by including env in the bi-cistronic vector.

For the construction of the new vector at first, an Akv-env was inserted downstream of the IRES-element in the zeo-IRES containing vector, as described in Example 1, giving rise to Bi-zeo-env vector. The spacer between IRES and env was constructed to be the same length as in EMCV but with an altered sequence holding a restriction recognition site Not I (see also FIG. 2). Translation efficiency of this IRES-env cassette was analysed in a complementation experiment with a GagPol expression construct. Transfer of the supernatant from a NIH3T3 cell culture transiently transfected with the vector Bi-zeo-env and the GagPol expression construct did not reveal any transduction events, implying a very low and difficult to detect translation efficiency of the env from the Bi-zeo-env. To test whether the spacer sequence has an influence on translation efficiency a further vector was constructed.

Therefore, a further bi-cistronic vector for the expression of Akv-env was constructed on the basis of Bi-zeo-neo (as described in Example 1) by substituting zeo with env. Efficient expression from an IRES-env translation cassette was subsequently attempted by using a spacer sequence as used for the construction of the IRES-neo cassette, as described in Example 1. This new IRES-env construct was inserted in a neo-expressing Akv-MLV vector, giving rise to Bi-neo-env. The inserted spacer differed from the IRES-neo spacer by three nucleotides in length and by minor alteration in sequence (compare spacer sequence of Bi-zeo-neo and Bi-neo-env in FIG. 2). When Bi-neo-env was tested in a complementation experiment with a GagPol expression construct transduction events were detected proving a functional env-translation.

For the, production of viral particles from these vectors a specialised packaging cell providing Gag/Pol proteins is needed, thereby completing the lack of structural genes on the viral vector.

Accordingly, this new vector system consists of a bi-cistronic retroviral vector, expressing a marker/effector gene and a functional env gene, and of a complementing cell line, designated a semi-packaging cell line, expressing GagPol-proteins. By expressing env from the vector, in contrast to ordinary transduction systems where env is expressed from the packaging cell line, superinfection interference is avoided and the bi-cistronic vector thereby becomes replication-competent within the semi-packaging cell culture. The new vector system combines attractive features from wt retroviruses and single-round of transduction systems by being capable of performing multiple rounds of infections, as wt viruses, and in the same time containing a heterologous gene, as ordinary transduction systems.

Construction of Semi-Packaging Cell Lines

The GagPol-expression in the semi-packaging cells is obtained from the Moloney-based CeB-construct (43). The translational control of CeB is performed from the Moloney-LTR. CeB has a major deletion in the 5'-untranslated region, which makes the RNA transcripts packaging deficient (42). 74-nt downstream of the pol stop-codon the bsr selectable marker, conferring resistance to blasticidin S, has been inserted. According to the authors bsr is expressed by reinitiation of translation after the upstream gagpol has been expressed. Selection of a CeB transfected cell culture with blasticidin S should thereby give high expression of GagPol.

CeB was transfected into murine NIH3T3 cells and human TE671 cells and initially selected with 5 μg/ml blasticidin S for 12 days. Subsequently the selectional level was stepwise increased to 10 μg/ml for 9 days, 20 μg/ml for 7 days and finally 40 μg/ml for 10 days in order to select for high producing cells among the pooled population of clones. The resulting ceil populations named NIHI/CeB and TE/CeB are used in the following analyses.

Complementation Analysis

The capability of the semi-packaging cell lines and the bi-cistronic Bi-neo-env vector to complement each other was analysed in a titer experiment with NIH3T3 cells as target cells. Bi-neo-env contains the full length 5'-untranslated region of Akv-MLV, as it was found that enclosure of the 3'-end of this region promoted an almost 3-fold increase in RNA expression level as compared to vectors including only the 5'-end of the region (containing the essential encapsidation sequence). Including this untranslated region in the vector may though give an enhanced risk of recombination between the packaging construct (CeB) and the bi-cistronic vector, as CeB contains the Moloney 3' part of the untranslated region. Titers at $3 \times 10^5$ and $4 \times 10^5$ CFU/ml were obtained, confirming that the constructs can complement each other and that the bi-cistronic vector is efficiently transferred to target cells. All the following analyses were performed with the NIH/CeB cells in combination with bi-cistronic vectors expressing ecotropic Env-proteins. Usage of the TE/CeB semi-packaging cell line in the new vector system will require expression of envelope proteins capable of mediating infection of human cells, such as amphotropic-Env or functional chimeric ecotropic envelopes displaying heterologous ligands capable of binding human cell surface receptors.

| Transduction efficiency | |
|---|---|
| Cell line | Titer (G418 CFU/ml) |
| NIH/CeB/Bi-neo-env | $4 \times 10^5$ |
| TE/CeB/Bi-neo-env | $3 \times 10^5$ |

Multiple Rounds of Infection with Bi-neo-env

To analyse if the Bi-neo-env vector was replication-competent within the NIH/CeB semi-packaging cell culture two different multiple rounds of infection procedures were performed. In the first procedure, virus-containing supernatant, containing Bi-neo-env, was transferred to NIHI/CeB cells ($8 \times 10^5$ cells in a 80 cm² dish) and after 24 hours G418 was applied. The semi-packaging cells were selected for 5–7 days with G418 and subsequently supernatant (crude from confluent cell populations, without G418) was added to uninfected NIH/CeB cells. This procedure was continuously followed for six rounds, resulting in passage one to six. In the other procedure, the Bi-neo-env was passaged for five rounds (passage one to five) without selecting for neo-expression. The infected NIH/CeB cells were in this procedure cultured for 7 days in the presence of 2 μg/ml polybrene and subsequently these infected NIH/CeB cells were mixed with uninfected NIH/CeB cells in a ratio of 1:10 (~$5 \times 10^4$ cells mixed with ~$5 \times 10^5$ cells), giving rise to the succeeding passage. Both procedures were initiated with crude supernatant from a Bi-neo-env transiently transfected BOSC23 packaging cell line (Pear et al. 1993). After each passage RNA was extracted from the cell cultures and Northern blot analysis was performed.

The Northern blot confirms that Bi-neo-env is replication-competent within the semi-packaging cell culture. Hybridisation with env- and neo-probes revealed a clear band corresponding to the vector size. This band is recognised in all of the passages where G418 were added, which was expected as G418 resistant cells appeared during selection. For the unselected passages (minus G418) the vector band can be recognised with equal intensity for all five passages indicating that the mini-viruses contained within the passage 1-cells not just have been diluted during the co-cultivation but also has spread to uninfected cells and thereby performed multiple rounds of infection. The Northern blot hybridised with an env-probe revealed, apart from the vector bands, additional bands in the two last passages in both the procedures. Two classes of bands can be recognised; (1) bands with a similar mobility as the wt Akv-spliced transcript, and (2) bands with slightly higher mobility than the wt Akv unspliced transcript. By analysis of the same Northern blot with a CeB-probe, bands corresponding to the expected unspliced and spliced CeB-transcripts can be seen. Apart from these bands the additional bands, seen with the env-probe, can also be recognised with the CeB-probe, showing that these RNA-transcripts also include sequences contained within the CeB construct.

To analyse if the replication potential of Bi-neo-env was retained during the procedures based on multiple rounds of infection a titer experiment with the initial cell cultures (passage 1) and the final cell cultures (passage 5 (−G418) and passage 6 (+G418)) was made. Surprisingly, a 30-fold improvement of the transduction efficiency was observed from the procedure with G418 selection (from $2 \times 10^5$ to $6 \times 10^6$ CFU/ml), whereas the transduction efficiency provided by the cells without G418 selection both in the initial and the final passage were found to be at a similar high level at around $7 \times 10^6$ CFU/ml.

| Transduction efficiency of selected and unselected Bi-neo-env after multiple rounds of infection | |
|---|---|
| NIH/CeB/Bi-neo-env | Titer (G418 CFU/ml)[a] |
| Passage 1, +G418 | $2 \times 10^5$ |
| Passage 6, +G418 | $6 \times 10^6$ |
| Passage 1, −G418 | $7 \times 10^6$ |
| Passage 5, −G418 | $8 \times 10^6$ |

[a]Values from a single experiment. Titer on NIH3T3 cells.

Replication-Competent Vectors

In light of the obtained results it could be speculated that replication-competent vectors have arose during the infection procedures. A recombinant virus with a splicing pattern similar to wt Akv-MLV would explain the additional transcripts in the Northern blot. However, these viruses would have a smaller genome size than wt Akv, as the RNA transcripts of these potential replication-competent vectors has a higher mobility than the wt RNA transcript, as judged by Northern blotting. A recombinant virus with efficient splicing, thereby giving a high env-expression, would also explain the improved transduction efficiency observed in the +G418 procedure, as it can be presumed that the env-expression from Bi-neo-env is below the optimal level, as the IRES-spacer sequence is suboptimal. Presence of such a recombinant virus with a high env-expression within the same semi-packaging cell as Bi-neo-env might thereby rescue the Env-production, resulting in a higher transduction efficiency of Bi-neo-env. The presence of potential replication-competent vectors within the cell cultures was tested by transferring crude supernatant to NIH3T3 cells ($8 \times 10^5$ cells in a 80 cm² dish), culturing the cells for 7 days and subsequently transferring crude supernatant from these NIH3T3 cell cultures to fresh uninfected NIH3T3 cells. If replication-competent vectors arose during the passages then they would be expected to infect not only the first NIH3T3 cell culture (rescue 1) but also the second (rescue 2). Cellular RNA from the rescue experiments was analysed by Northern blotting.

According to the Northern blot (env-probe) of RNA from several of the passages there are no replication-competent vectors within the semi-packaging cell cultures. For the rescue 1-cell cultures an env-transcript-pattern similar to the pattern in the corresponding semi-packaging cell culture can be detected, which is expected as these cells are transduced with virus particles from cell lines with packaging cell capacity. In the rescue 2-cell cultures env-expressing transcripts are absent, indicating that NIH3T3 cells had not been infected by recombinant viruses.

Env-expressing rescue vector. The additional bands recognised in the final passages of the multiple rounds of infection procedures may be explained by the presence of an env-expressing rescue vector. The env-expression is probably suboptimal in the bi-cistronic Bi-neo-env vector and it can therefore be suggested that a vector with an improved Env-production would have higher replication efficiency than Bi-neo-env. Such a new minivirus was constructed where the leader from the IRES element to the envelope gene is the same as the one used for the improved translational cassette in the maxivirus construct VIRAGFPM (Table1). This minivirus construct is named Bi-neo-envMO and used in the example with the two amino acid library described below. In one experiment minivirus containing supernatant with this linker was diluted up to one million fold to ensure single copy colonies. These colonies sustained normal titers of minivirus, arguing that single copy cell clones support high-titer production of infectious miniviruses. Furthermore, single colonies from single copy clones with different combinatorial amino acid alterations selected from a functional two amino acid library also sustained titers in the range of $10^4$ to $10^6$ (see table 2).

A vector with higher replication efficiency than the initial vector will during multiple passages be expected to become dominant in the cell population and thereby suppress the spread of the initial vector. For the infection procedure with G418 selection this hypothetical env-expressing rescue vector will not become totally dominant in the vector population, unless it expresses neo, as it has to be present in the cells together with Bi-neo-env, which supplies the G418 resistance. For the infection procedure without G418 addition this vector may become dominant if the passages were continued beyond passage 5, as a drastic increase in the supposed recombinant vector transcripts is observed from passage 4 to passage 5 and therefore may continue its expansion in passage 6.

This model assumes that two recombination events have happened between the semi-packaging construct and the bi-cistronic vector, giving rise to a functional retroviral vector with a spliced transcript encoding the env-gene. Env-production from spliced transcripts will probably be more efficient than from the suboptimal IRES-env translation cassette, thereby giving the recombinant vector an advantage as compared to Bi-neo-env. The recombination between the two constructs can either have happened during the reverse transcription process or been mediated by cellular mechanisms (DNA recombination). Patience et al. (1998) found that CeB-transcripts are packaged into virus particles at a low frequency, which thereby makes them a potential recombination source during reverse transcription. The Moloney-based CeB-construct contains a 53-nt sequence upstream of gag which share 55% sequence similarity with the corresponding region in Bi-neo-env. But as the genome sizes of the suspected recombinant vectors all are smaller than wt-Akv and as non of the vectors are replication-competent in NIH3T3 cells it may be suggested that the 5' recombination events between Bi-neo-env and CeB have happened from around 5'-neo to somewhere inside gag-giving a gag-deficient phenotype. The 3'-end of Moloney-pol has 88% sequence homology with the 5'-Akv-env. Recombination events between these homologous sequences or between the Moloney pol-sequence downstream of the splice acceptor site and the IRES-sequence may render a splicing phenotype, due to reconstitution of both splice sites, and thereby provide an efficient env-expression.

In the infection procedure with addition of G418 a 30-fold improvement in transduction efficiency was observed after six passages. An env-expressing rescue vector can explain the elevated efficiency as a higher Env-expression level in the producer cells probably would give an enhanced production of virus particles. For the infection procedure without G418 addition the same high transduction level was observed in the first and the last passage. The performed analysis cannot explain this result but continuous reinfections from neighbouring cells in combination with a prolonged latency for saturation of the ecotropic receptor, due to the suboptimal IRES-env translational cassette, may contribute to the explanation.

Multiple Rounds of Infection with Bi-EGFP-env

To enable a more direct examination of viral spread in semi-packaging cells an EGFP-expressing bi-cistronic vector (Bi-EGFP-env) was included in the study. Multiple rounds of infection analysis were performed by supplying supernatant from BOSC23 cells transiently transfected with Bi-EGFP-env to NIH/CeB ($8 \times 10^5$ cells in a 80 cm$^2$ dish), culturing the cells for 14 days with 2 µg/ml polybrene and subsequently transferring crude supernatant to uninfected NIH/CeB cells. Only three passages were performed as the fraction of EGFP-expressing cells drastically decreased following each passage. For all three passages, examination of the cells for EGFP-expression by fluorescence microscopy revealed an increase in green cells until day 7–10 after which a constant ratio of EGFP-expressing to non-expressing cells was observed.

Flow cytometric analysis performed with cells from the three passages shows a EGFP-expressing fraction of around 50% for passage 1, below 10% for passage 2 and less than 1% in passage 3. It was found that the percentage of EGFP-expressing cells is rapidly decreasing during the passages.

In order to analyse the genomic integrity of the Bi-EGFP-env vector during the multiple passages, RNA was extracted in the end of each passage and Northern blot analysis with an env-probe was performed. The RNA transcript corresponding to full-length Bi-EGFP-env can only very weakly be detected in passage 1 and passage 2, while a band with higher mobility can be clearly detected in all three passages. In passage 3, clear bands, which are similar in size to the bands comprising the assumed recombination-vector in the Bi-neo-env experiments, can also be seen.

The Northern blot analysis together with the EGFP-expression data show that Bi-EGFP-env is poorly replicating in the semi-packaging cells. The vector RNA is almost undetectable by Northern blotting, while RNA corresponding to a smaller size vector appears with a high intensity. This suggests that the Bi-EGFP-env vector contains an instability element impairing the replication efficiency. The presumed vector with a genome size around 1-kb smaller than Bi-EGFP-env is found in a high amount in all three passages. This vector may have arisen after a major deletion within the EGFP-IRES region, which may result in a vector where env is translated from a 5'-position, thereby providing efficient env-translation. The explanation for the additional bands in passage 3 may be the same as for the similar bands recognised in the Bi-neo-env experiments.

In Vivo Selection of a Two Amino Acid Randomised Envelope Library by the New Vector System The mini-virus has a size, which is manageable by PCR-techniques and introduction of randomised sequences by PCR is therefore a potential application. Genomic libraries constructed by PCR will necessarily consist of linearised DNA-fragments and in order to analyse if this feature reduces the transduction efficiency compared to circular DNA a transient transduction experiment was performed. This analysis revealed no difference in the transduction efficiency.

| Transduction efficiency of circular versus linearised Bi-neo-env | |
|---|---|
| Bi-neo-env[a] | Titer[b] (G418 CFU/ml) |
| Circular | $1.4 \times 10^6$ |
| Linearised[c] | $1.3 \times 10^6$ |

[a]BOSC23 cells transiently transfected with Bi-neo-env.
[b]Titer experiment performed with NIH3T3.
[c]Linearised with NdeI and SspI restriction enzymes.

Several amino acids in the variable region A domain of the surface protein is known to be involved in the receptor binding and even minor alterations in the peptide sequence in this domain have been shown to render the envelope-protein nonfunctional (39, 40). MacKrell et al. (1996) showed that, among others, an arginine and an aspartate residue (position 83 and 84) in Mo-Env are very important for the envelope mediated infectivity.

To prove the feasibility of the new vector system these two amino acids were randomised by an overlap extension procedure and selected in the new vector system. Randomisation of two amino acids should give a vector library with 400 ($20^2$) different phenotypes. Approximately 500 ng of vector library constructs were transiently transfected (with 10 kg salmon sperm carrier DNA) into BOSC23 packaging cells. Crude supernatant was added to a NIH/CeB cell culture. If these transduced cells only contain a single vector genome, the mutated Env-protein coating the virus particles will reflect the env-encoding vector sequence encapsidated in the particle and genotype will thereby follow phenotype.

In order to discover functional phenotypes, supernatant from the pooled colonies was added to uninfected NIH/CeB cells and challenged with G418 selection. After G418 selection a number of colonies were isolated of which some are shown in table 2. The genome structure of the envelope gene of these minivirus was revealed by PCR amplifying the integrated miniviral provirus and sequencing the revelant part (table 2). The infectious capability of these mutant envelopes was revealed by performing titer assay of said cell clones harboring single copy mutant miniviral proviruses (table 2). In conclusion there is a preference for aspartic acid in the second position of the randomized sequence, although other hydrophilic amino acids are also tolerated. Said experiment is proof of principle for using minivirus as tool for selection of mutated or functionally altered envelope genes.

Example 3

Animal Experiments

A construct with an optimal translational initiation was selected. Animals were infected with the construct VIRAG-FPM and the number of infected and EGFP-positive cells was scored. It was shown that VIRAGFPM infects the cells in a high rate.

3.1 Optimization of the Leader between the IRES EMCV IRES Element and Translational Start of the Heterologous Gene To optimize internal translational initiation from the EMCV IRES element several different leaders (see Table 1)

were analyzed for EGFP expression in the context of the replication competent Akv murine leukemia virus. In two constructs, VIRAGFPC and VIRAEGFP (see Table 1), polylinkers with convenient restriction sites were inserted with the polylinker in VIRAGFPC being derived from the Clontech construct pIRES-EGFP. Both viruses showed a 10-fold decrease in flourescence by flow cytometry analysis as compared to the best construct tested, VIRAGFPM. This leader contains a NcoI site at the translational start site of the heterologous gene. The rest of the leader resembles the original leader from EMC virus except from one point mutation at translational start codon 10 in the original EMCV IRES element, see table of sequences. This leader has previously been described by Morgan et al. (1992): Nucl.Acids Res. 20(6): 1293–9.

| Virus (constructs see Table 1) | Translational efficiency of IRES construct | Titer |
| --- | --- | --- |
| VIRAGFPM | 10-fold X (Flow) | $10^5$–$10^6$ |
| VIRAGPPC | X (estimated) | like VIRAEGFP |
| VIRAEGPP | X (Flow) | $10^5$–$10^6$ |
| AENGFMK2 | 10-fold X (estimated) | $10^6$ |
| AKENGFML | 10-fold X (estimated) | <10 |

3.1 In Vivo Performance of VIRAGFPM $10^4$ infectious units per ml in 100 microliter were injected intraperitoneally. Animals were analyzed on day 1, 4, 7, 14, 33 and 60. Because the small size of the pups, spleens of 6 animals were mixed on day 1 and 3 animals on day 4 and day 7. On day 14, 33, 60 one animal was analyzed in each experiments.

day 1: No EGFP positive cells
day 4: 50 to 75% EGFP positive cells
day 7: 50 to 80% GFP positive cells
day 14: 0.5% GFP positive cells
day 33 and day 60 no positive cells except for 1 animal which showed 22% GFP positive cells.

Titer Experiment

Blood viremia was analysed using two assays. In the first one, *Mus dunni* cells were infected using serial dilutions of blood samples and EGFP positive cells were scored. This permits assay of unrearranged maxivirus. In the second one, Mus dunni cells were also infected using serial dilutions of blood, but viruses were scored using a flourescence immunoassay involving the anti-env monoclonal antibody 83A25 (Evans et al. J. Virol. 64, 6176–83, 1990). This permits assay of both unrearranged vectors and vectors which have deleted EGFP.

| Day | Cfu/ml blood | NaCl | Experiment 1 | Experiment 2 |
| --- | --- | --- | --- | --- |
| 1 | 83A25 | — | — | — |
|   | EGFP  | — | — | — |
| 4 | 83A25 | — | $8 \times 10^3$ | $5 \times 10^3$ |
|   | EGFP  | — | $4 \times 10^3$ | $2 \times 10^3$ |
| 7 | 83A25 | — | $2 \times 10^5$ | $1 \times 10^5$ |
|   | EGFP  | — | $2 \times 10^2$ | $2 \times 10^3$ |
| 14 | 83A25 | — | $3 \times 10^5$ | $1 \times 10^5$ |
|    | EGFP  | — | — | $4 \times 10^{1(a)}$ |
| 33 | 83A25 | — | $2 \times 10^5$ | $1 \times 10^5$ |
|    | EGFP  | — | — | $1 \times 10^{2(a)}$ |
| 60 | 83A25 | — | $2 \times 10^5$ | $3 \times 10^5$ |
|    | EGFP  | — | — | — |

Each experiment is an average of two animals
(a)One animal out of two

The decline in EGFP positive cells after day 7 is probably the result of deletions of parts of the IRES-EGFP element in VIRAGFPM. These revertant viruses have been characterized for VIRAGFPM in cell culture and consist of viruses where 50 to 100 nucleotides of the inserted IRES-EGFP fragment is remaining at the insertion site. This deletion of the majority of the IRES-EGFP fragment results in a restoration of the balance between the spliced and the unspliced viral RNA (Jespersen et al 1999). This is reflected in the titer experiment where the antibody 83A25 detects the envelope of the revertans as well as VIRAGFPM. In this experiment the EGFP titer declines after day 7 but the titer estimated from the envelope recognizing antibody remains high throughout the experiment.

In conclusion VIRAGFPM establishes a high infection rate during the first days after injection (up to 80% of EGFP positive spleen cells after day 7). After day 7, the VIRAGFPM is overtaken most likely by a revertant of VIRAGFPM that restores splicing giving the revertant virus a growth advantage. Previous results also indicate that AENGFMK2 works as well as VIRAGFPM.

Example 4

Cloning Capacity of Maxiviruses

The experiments described here are designed to analyze the maximal packaging/transduction capacity of MLV-based vectors and are focussed on the Akv-MLV strain.

A wild type Akv-MLV having a genome size of 8.4 kb, is analyzed for maximal encapsidation/transduction capacity after increasing the RNA genome size by insertion of heterologous sequences of different lengths. These new constructs are analyzed for transduction capability to target cells, encapsidation into the virus particles and for a possible packaging rescue by formation of heterodimers with a small size retroviral vector.

The System

Wild type Akv-MLV having a genome size of 8.4 kb was analyzed for maximal encapsidation capacity after insertion of a 1.4 kb insert, containing the internal ribosomal entry site (IRES) plus the neomycin resistance gene (neo) as a selectable marker, in the U3 region of the 3' viral LTR giving a pAkvBi-neo construct (maxi-virus). Sequences of 1 to 4 kb of exogenous λ DNA were inserted in the Not I sites of the U3 region in the 3' viral LTR in front of the IRES-neo and 1 and 3 kb λ DNA sequences were inserted in the Xho I sites in the pol gene giving Mega-vectors. The transduction efficiency of the constructs was tested in a retroviral transduction system and the vector pBi-Zeo-neo was used as a control for this purpose (See FIG. 3 for genome structures).

BOSC 23 cells, a human packaging cell line, were transiently transfected with the various constructs. Virus supernatant 48 to 72 hours after transfection was used to infect NIH3T3 cells by end-point dilution. The presence of the neo gene allowed selection, 24 hours later, of infected cells among target cells by addition of G418 to the cell medium. Titer was measured two weeks after selection and the results are presented in FIG. 3 and the legend to FIG. 3.

Since it is not known whether this packaging size limit relies on the individual RNA sizes or the total amount of RNA that can be packed, a co-packaging experiment was carried out where the constructs holding the different inserts were co-packed with a small helper vector such as pMSS5 having a size of 3 kb. Because RNA is packed as dimers into the virus particles, maybe two RNA molecules of 14 kb, for the largest vector, are not encapsidated, but when two RNA molecules of 14 and 3 kb are co-packed, the efficiency of the virus containing this heterodimer could be increased. The helper vector pMSS5, carrying the phleomycin resistance gene, was used in transfection and later transduction of BOSC 23 and NIH 3T3 cells in order to determine if the transduction efficiency could be improved. The human packaging cell line BOSC 23 was used in the experiment to avoid the presence of small endogenous vectors capable of rescuing the constructs and interfering in the co-packaging process. BOSC 23 cells were transiently transfected with controls, pAkvBi-neo and Mega-vectors plus the pMSS5 vector. Virus supernatant 48 to 72 hours after transfection was collected to infect NIH 3T3 cells and 24 hours after infection selection with G418 and Phleomycin was performed for neo and zeo resistant genes. Titer was measured two weeks after selection and results are presented in FIG. 3.

In order to determine how the exogenous λ DNA influences in the efficiency of the vectors, deletions were made in the middle of the genome for the largest vector, Mega 4 kb, as a control, and transduction capability of the new constructs was tested. Results are shown in FIG. 3

Results

The transduction efficiency of pAkvBi-neo was analyzed using a pBi-Zeo-neo as a control. The results showed that this pAkvBi-neo construct was as efficient as the controls, with a titer value of 10(5) CFU/ml. When the Mega-vectors were analyzed for transduction capability, it was observed that the efficiency was gradually reduced from 10(5) to 10(1) when the sizes of the λ DNA inserts where increased from 1 to 4 kb (FIG. 3).

After the titer was measured, transduced NIH 3T3 cells were harvested to analyze RNAs by a Northern blot assay. Wild-type Akv-MLV and pBi-Zeo-neo were used as controls. It was observed that the pAkvBi-neo construct, 1.4 kb larger than the wild-type, was efficiently transduced and no deletions were found. When RNAs from Mega-vectors were analyzed, the vector containing the 1 kb λ DNA insert, 2.4 kb larger than the wild-type, was transduced and presented no deletions while for the rest of Mega-vectors, Northern blot results showed revertants coming up after two weeks of selection.

To analyze the revertants observed in the Northern blots, a transduction experiment was performed where all the constructs were transiently transfected into BOSC 23 cells. 48 hours after transfection, virus supernatant was used to transduce NIH 3T3 cells. No selection was applied in order to avoid the possibility of the revertants coming up. RNA from BOSC 23 cells was recovered 4 days after transfection and from target NIH 3T3 cells, 2 days and 1 week after transduction, for Northern blot analyses. To enable more direct examination of viral spread through cell cultures, an EGFP expressing virus, AkvBi-EGFP, was included in the experiment. Bi-zeo-neo and Akv-wt, together with AkvBi-EGFP, were included as controls. Two major RNA transcripts, an unspliced and a spliced mRNA, in BOSC 23 cells analyses were expected and observed for AkvBi-EGFP, Akv-wt and AkvBi-neo. For Mega-vectors, an unspliced and spliced mRNA 1 kb and 2 kb larger than AkvBi-neo, corresponding to the Mega-vector holding the 1 kb and 2 kb λ DNA inserts, was very weakly observed in the packaging cells. Results from the target cells showed the Mega-vector with the 1 kb λ DNA insert to be expressed while for Mega-2 kb vector, no band was detected (Data not shown).

When analyzing transduction efficiency for the Mega-vectors with deletions, pBi-zeo-neo and pAkvBi-neo were included as controls, with titer values of 10(7) CFU/ml. Transduction efficiency for the Mega 4 kb-vector with a deletion of 1.5 kb (Mega 4 kb-AflII) was drastically reduced, the titer went down from 10(7) to 10(1) and for the Mega 4 kb-vector that contained the 5 kb deletion (Mega 4 kb-AflII-BstEII), no colonies were observed.

RNA from transduced NIH 3T3 cells was harvested and studied by a Northern Blot assay. RNA analyses from the controls showed that pBi-zeo-neo and pAkvBi-neo were transduced with a high efficiency and no deletions were observed, but when RNA for the vector with deletions was analyzed, very weak bands were detected.

Conclusions

This example study the maximal packaging capacity of retroviral vectors with a focus on Akv-MLV vectors.

Replication-competent MLV-based vectors were constructed for analysis of transduction capability. The results obtained showed that these vectors could produce infectious virus particles, indicating that the inserts did not interfere with the replication functions of the virus. However, a restriction in transfer capability was encountered when insert size was further increased. It was observed that the transduction efficiency of these MLV-based vectors decreased when the RNA genome size was increased beyond 10 kb.

REFERENCES

1. Barnier J. V., M. Marx, P. Dezelee, D. Laugier, F. Poirier, G. Calothy, J. Hillova, and M. Hill. 1990. Transformation-defective mutants with 5' deletions of the src gene are frequently generated during replication of Rous sarcoma virus in established quail fibroblasts. Virology 177:505–514.
2. Barsov, E. V. and S. H. Hughes. 1996. Gene transfer into mammalian cells by a Rous sarcoma virus-based retroviral vector with the host range of amphotropic murine leukemia virus. J. Virol. 70: 3922–3929.
3. Chen, B. -F., L. -H. Hwang, and D. -S. Chen. 1993. Characterization of a bicistronic retroviral vector composed of the swine vesicular disease virus internal ribosome entry site. J. Virol. 67:2142–2148.
4. Chomczynski, P., and N. Sacchi. 1987. Single-step method of RNA isolation by acid guanidium thiocyanate-phenol-chloroform extraction. Anal. Biochem. 162:156–159.
5. Coulombe, J., Y. Avis, and D. A. Gray. 1996. A replication-competent promoter-trap retrovirus. J. Virol. 70:6810–6815.
6. Dillon, P. J., J. Lenz, and C. A. Rosen. 1991. Construction of a replication-competent murine retrovirus vector expressing the human immunodeficiency virus type 1 tat transactivator protein. J. Virol. 65:4490–4493.
7. Eiden M V, Farrell K and Wilson C A, 1994, Glycosylation-dependent inactivation of the ecotropic murine leukemia virus receptor. J. Virol. 68: 626–631.
8. Murphy & Goff 1989, Construction and analysis of deletion mutations in the U5 region of MoMLV: effects on RNA packaging and reverse transcription. J Virol 63, 319–327

9. Emerman M., and H. M. Temin. 1984. Genes with promoters in retrovirus vectors can be independently suppressed by an epigenetic mechanism. Cell 39:459–467.

10. Foster, D. A., and H. Hanafusa. 1983. A fps gene without gag gene sequences transforms cells in culture and induces tumors in chickens. J. Virol. 48:744–751.

11. Graham, F. L., and A. J. van der Eb. 1973. A new technique for the assay of infectivity of human adenovirus 5 DNA. Virology 52:456–467.

12. Hughes, S., and E. Kosik. 1984. Mutagenesis of the region between env and src of the SR-A strain of Rous sarcoma virus for the purpose of constructing helper-independent vectors. Virology 15:89–99.

13. Hughes, S. H., J. J. Greenhouse, C. J. Petropoulos, and P. Sutrave. 1987. Adaptor plasmids simplify the insertion of foreign DNA into helper-independent retroviral vectors. J. Virol. 61:3004–3012.

14. Jang, S. K., and E. Wimmer. 1990. Cap-independent translation of encephalomyocarditis virus RNA: Structural elements of the internal ribosome entry site and involvement of a cellular 57-kD RNA-binding protein. Genes Dev. 4:1560–1572.

15. Gilmartin et al., 1995, CPSF recognition of an HIV-1 mRNA 3'prosessing enhancer: multiple sequences contacts involved in Poly(A) site definition. Genes Dev 9: 72–83.

16. Jorgensen, P., T. Mikkelsen, F. S. Pedersen, and N. O. Kjeldgaard. 1988. An MuLV transmission vector system designed to permit recovery in E. coli of proviral and cellular flanking sequences. Virus Genes 1:221–233

17. Koo, H. M., A. M. C. Brown, R. J. Kaufman, C. M. Prorock, Y. Ron, and J. P. Dougherty. 1992. A spleen necrosis virus-based retroviral vector which expresses two genes from a dicistronic mRNA. Virology 186: 669–675.

18. Kormbluth, S., F. R. Cross, M. Harbison, and H. Hanafusa. 1986. Transformation of chicken embryo fibroblasts and tumor induction by the Middle T antigen of Polyomavirus carried in an avian retroviral vector. Mol. Cell. Biol. 6:1545–1551.

19. Lee A. H., J. M. Han, and Y. C. Sung. 1997. Generation of the replication-competent human immunodeficiency virus type 1 which expresses a jellyfish green fluorescent protein. Biochem. Biophys. Res. Commun. 233:288–92.

20. Lenz, J., D. Celander, R. L. Crowther, R. Patarca, D. W. Perkins, and W. A. Haseltine. 1984. Determination of the leukemogenicity of a murine retrovirus by sequences within the LTRs. Nature 308:467–470.

21. Lenz, J., R. L. Crowther, A. Straceski, and W. A. Haseltine. 1982. Nucleotide sequence of the Akv env gene. J. Virol. 42:519–529.

22. Lobel, L. I., M. Patel, W. King, M. C. Nguyen-Huu, and S. P. Goff. 1985. Construction and recovery of viable retroviral genomes carrying a bacterial suppressor transfer RNA gene. Science 228:329–332.

23. Lovmand, J., A. B. Sorensen, J. Schmidt, M. Ostergaard, A. Luz, and F. S. Pedersen. 1998. B-cell lymphoma induction by Akv murine leukemia viruses harboring one or both copies of the tandem repeat in the U3 enhancer. J. Virol. 72:5745–5756.

24. Graveley & Gilmartin, 1996, A common mechanism for the enhancement of mRNA 3' processing by U3 sequences in two distantly related lentiviruses, J Virol 70: 1612–1617.

25. Lund, A. H., M. Duch, J. Lovmand, P. Jorgensen, and F. S. Pedersen. 1993. Mutated primer binding sites interacting with different tRNAs allow efficient murine leukemia virus replication. J. Virol. 67:7125–7130.

26. Murakami, M., H. Watanabe, Y. Niikura, T. Kameda, K. Saitoh, M. Yamomoto, Y. Yokouchi, A. Kuroiwa, K. Mizumoto, and H. Iba. 1997. High-level expression of exogenous genes by replication-competent retrovirus vectors with an in internal ribosomal entry site. Gene 202: 23–29.

27. Ogawa K., R. Shibata, T. Kiyomasu, I. Higuchi, Y. Kishida, A. Ishimoto, and A. Adachi. 1989. Mutational analysis of the human immunodeficiency virus vpr open reading frame. J. Virol. 63:4110–4114.

28. Paludan, P., H. Y. Dai, M. Duch, P. Jorensen, N. O. Kjeldgaard, and F. S. Pedersen. 1989. Different relative expression from two murine leukemia virus long terminal repeat in unintegrated transfected DNA and in integrated retroviral vector proviruses. J. Virol. 63:5201–5207

29. Pear, W. S., G. P. Nolan, M. L. Scott, and D. Baltimore. 1993. Production of high-titer helper-free retroviruses by transient transfection. Proc. Natl. Acad. Sci. USA 90:8392–8396.

30. Petropoulos, C. J., and S. H. Hughes. 1991. Replication-competent retrovirus vectors for the transfer and expression of gene cassettes in avian cells. J. Virol. 65:3728–3737.

31. Rees, S., J. Coote, J. Stables, S. Goodson, S. Harris, and M. G. Lee. 1996. Bicistronic vector for the creation of stable mammalian cell lines that predisposes all antibiotic-resistant cells to express recombinant protein. Bio-Techniques 20:102–110.

32. Reik, W., H. Weiher, and R. Jaenisch. 1985. Replication-competent Moloney murine leukemia virus carrying a bacterial suppressor tRNA gene: Selective cloning of proviral and flanking host sequences. Proc. Natl. Acad. Sci. USA. 82:1141–1145.

33. Sambrook, J., E. F. Fritsch, and T. Maniatis. 1989. Molecular cloning: a laboratory manual, $2^{nd}$ ed. Cold Spring Harbor Laboratory, N.Y.

34. Schwartz, D. E., R. Tizard, and W. Gilbert. 1983. Nucleotide sequence of Rous sarcoma virus. Cell 32:853–69.

35. Sodroski J., W. C. Goh, C. Rosen, A. Tartar, D. Portetelle, A. Burny, and W. Haseltine. 1986. Replicative and cytopathic potential of HTLV-III/LAV with sor gene deletions. Science 231:1549–1553.

36. Stuhlmann, H., R. Jaenisch, and R. C. Mulligan. 1989. Construction and properties of replication-competent murine retroviral vectors encoding methotrexate resistance. Mol. Cell. Biol. 9:100–108.

37. Stuhlmann, H., R. Jaenisch, and R. C. Mulligan. 1989. Transfer of a mutant dihydrofolate reductase gene into pre- and postimplantation mouse embryos by a replication-competent retrovirus vector. J. Virol. 63:4857–4865.

38. Van Beveren, C. 1985. In R. Weiss, N. Teich, H. Varmus, and J. Coffin (ed.), RNA tumor viruses, $2^{nd}$ ed., supplements and appendices. Cold Spring Harbor Laboratory, Cold Spring Harbor, N.Y.

39. Weiss, R., N. Teich, H. Varmus, and J. Coffin (ed.). 1985. RNA tumor viruses, $2^{nd}$ ed., supplements and appendices, chapter 4. Cold Spring Harbor Laboratory, Cold Spring Harbor, N.Y.

40. MacKrell et al. 1996, Identification of a subdomain in the Moloney murine leukemia virus envelope protein involved in receptor binding. J. Virol. 67: 7125–7130.
41. Bae et al. 1997, Functional dissection of the Moloney murine leukemia virus envelope protein gp 70. J. Virol. 71: 2092–2099.
42. Patience et al., 1998, Packaging of endogenous retroviral sequences in retroviral vectors produced by murine and human packaging cells. J. Virol. 72: 2671–2676.
43. Cosset et al. 1995, High-titer packaging cells producing recombinant retroviruses resistant to human serum. J. Virol. 69: 7430–7436.
44. Adam et al., 1991, Internal initiation of translation in retroviral vectors carrying picornavirus 5' nontranslated regions. J. Virol. 65:4985–4990;
45. Yin & Hu, 1999, Insertion of sequences into the 3' untranslated region of a replication-competent spleen necrosis virus vector disrupts env gene expression. Arch Virol 144, 73–87;
46. Barker et al., 1991, Nonsense codons within the RSV gag gene decrease the stability of unspliced viral RNA. Mol Cell Biol 11: 2760–2768;
47. Barker et al, 1994, RSV RNA stability requires an open reading frame in the gag gene and sequences downstream of the gag/pol junction. Mol Cell Biol 14: 1986–1996.
48. Bray et al., 1994, A small element of the Mason-Pfizer monkey virus genome makes HIV-1 expression and replication rev-independent. Proc Natl Acad Sci USA 91:1256–1260.
49. Miller & Buttimore, 1986, Mol Cell Biol 6(8): 2895–902.
50. Mann et al., 1983, Construction of a retrovirus packaging mutant and its use to produce helper-free defective retrovirus. Cell 33: 153–159.
51. Miller et al., 1991, Construction and properties of retrovirus packaging cells based on gibbon ape leukemia virus. J. Virol. 65: 2220–2224.
52. Miller & Rosman, 1989, Improved retroviral vectors for gene transfer and expression. Biotechniques 7(9): 980.
53. Price et al., 1987, Proc Natl Acad. Sci USA 84: 156–160
54. C. Torrent et al., Human Gene Ther. 7:603–612 (1996);
55. M. Lastra et al., Human Gene Ther. 8:1855–1865 (1997);
56. S. Vagner et al., J. Biol. Chem. 270:20376–83 (1995);
57. C. Berlioz et al., J. Virol. 69:6400–07 (1995);
58. C. Berlioz and Darlix, J L. J. Virol. 69:2214–22 (1995)

TABLE 1

Figure 1B:
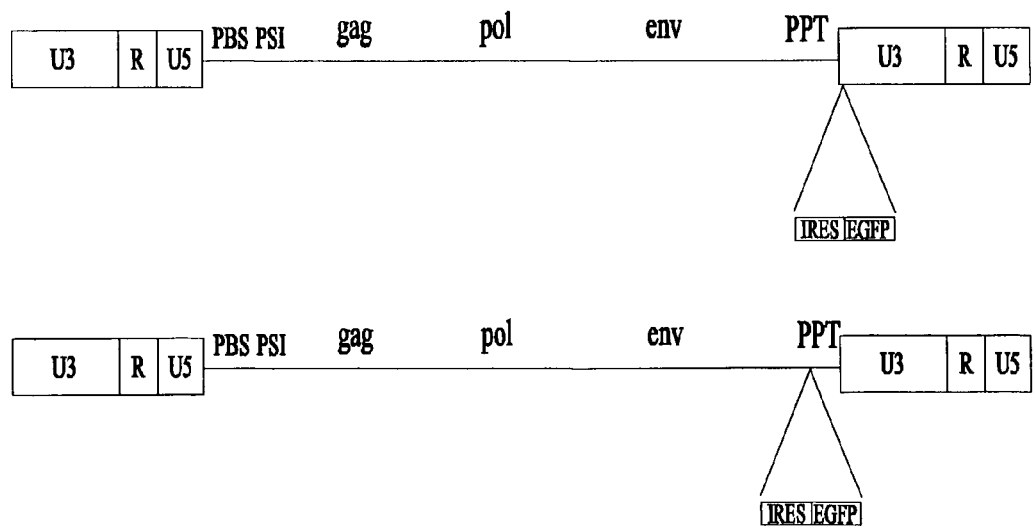

Sequences and constructs (see also FIG. 1B)

Constructs inserted into the U3 region of the 3'-LTR

EMV IRES:
CACGATGATAAT-----------------------------------------ATGCC (VIRUS)

VIRAGFPM: Leader between IRES and EGFP startcodon from Morgan et al. (1992): Nuci. Acid. Res. 20(6): 1293-9:
CACGATAATACC-----------------------------------------ATGGTG (EGFP)

VIRAGFPC: Leader between IRES and ECFP startcodon from Clontech:
CACGATGATAAGCTTGCCACAACCCGGGATCCACCGGTCGCCACC---------ATGGTG (EGFP)

VIRAEGFP: Leader between IRES and EGFP startcodon polylinker/M&E:
CACGATTGCCGCGTGTGGCCTCGAACACCGAGCGACCCTGCAGCCGCGGTCGACATGGTG (EGFP)

Constructs inserted into the Polypurine track (PPT) before the 3'-LTR

Wildtype
EnvCACGTGAATAAAAGATTTTATTCAGTTTACAGAAAAGGGGG-U3

AENGFMK2:
EnvCACGGGAATAAAAG-PL-IRES-EGFP-PL-CTTAAGACAATAGAAGATTGTAAATCACGTGAAT
AAAAGATTTTATTCAGTTTACAGAAAGAGGGGGG-U3

AKENGFML:
EnvCACGGGAATAA-IRES-EGFP-PL-AAGATTTTATTCAGTTTACAGAAAGAGGGGGG-U3

Relevant constructs from literature

Wildtype SNV:
TACCCTAGGTCAATGGTTTGACCA-PPT

Gélinas and Temin 1986: Proc. Natl. Acad. Sci 9211-9215
TACCCTAGGTCGATGGTCTAAGAATTCTCGAGTCTAGATCGATCGAATTCCTAGGTCAATGGTTTGAC
CA-PPT Yin and Hu (1999): Archives of Virology 144: 73–87:
TACCCTAGGTCGATGGTCTAAGAATT-IRES-Hygro/neo-AATTCTCGAGTCTAGATCGATCGAAT
TCCTAGGTCAATGGTTTGACCA-PPT

TABLE 2

| Number of isolated colonies | Incorporated codons | Translated amino acids | Titer on NIH3 |
|---|---|---|---|
| 1 | AGAGAT | Arg-Asp (wt) | $2.8 * 10^4$ |
| 1 | CGTGAT | Arg-Asp | $5 * 10^5$ |
| 2 | GAAGAT | Gly-Asp | $1.4 * 10^5$ $2.2 * 10^5$ |
| 1 | ACTGAT | Thr-Asp | $1.6 * 10^6$ |
| 2 | TCTGAT | Ser-Asp | $2 * 10^6$ $1 * 10^4$ |
| 1 | ATTGAT | Ile-Asp | $2.6 * 10^5$ |
| 1 | ATTAAT | Ile-Asn | $3.6 * 10^6$ |
| 1 | CTTGAG | Leu-Glu | $2.4 * 10^5$ |

TABLE 2-continued

| Number of isolated colonies | Incorporated codons | Translated amino acids | Titer on NIH3 |
|---|---|---|---|
| 4 | AGTCAT | Ser-His | $3.4 * 10^4$ $3 * 10^5$ $6.4 * 10^5$ -------- |
| 1 | CGTTCG | Arg-Ser | $3 * 10^5$ |
| 1 | GCTACT | Ala-Thr | $3.2 * 10^5$ |
| Control | AGAGAT | Arg-Asp | $5.6 * 10^6$ |

We claim:

1. A retroviral vector comprising a complete retroviral genome wherein at least all genes essential for replication of the retrovirus remain functional, said vector additionally comprising a heterologous nucleic acid sequence preceded by a heterologous internal ribosome entry site IRES inserted into a long terminal repeat region of said retroviral vector resulting in the translation of said sequence under the control of the IRES.

2. A replication-defective retroviral vector comprising a gene encoding a protein which is capable of initiating infection, wherein said gene is under translational control of a heterologous internal ribosome entry site IRES.

3. The retroviral vector according to claim 2 wherein the gene encoding the protein which is capable of initiating infection is an env gene.

4. The retroviral vector according to claim 3 comprising a heterologous env gene.

5. The retroviral vector according to claim 4 wherein env and the retroviral vector are from different species, subspecies, subtypes or clades.

6. The retroviral vector according to claim 2 wherein gag is additionally included in the vector.

7. The retroviral vector according to claim 2 wherein pol is additionally included in the vector.

8. The retroviral vector according to claim 2 wherein the vector includes gag or pol preceded by an additional IRES or by a promoter and/or enhancer element.

9. The retroviral vector according to claim 2 comprising in addition a heterologous gene.

10. The retroviral vector according to claim 9 wherein said heterologous gene is expressed under the control of an additional IRES or by a promoter and/or enhancer element.

11. The retroviral vector according to claim 2 wherein the IRES is inserted into a Long Terminal Repeat LTR.

12. The retroviral vector according to claim 11 wherein the IRES is inserted in the U3 region of the LTR.

13. The retroviral vector according to claim 12 wherein the IRES is inserted in the U3-region of the 3' LTR.

14. The retroviral vector according to claim 12 wherein the IRES is inserted in the U3 region between inverted repeats and transcription-regulatory elements thereof.

15. The retroviral vector according to claim 2 wherein the IRES is inserted outside a long terminal repeat LTR.

16. The retroviral vector according to claim 15 wherein the IRES is inserted between the end of an env gene and the 5' end of the 3' LTR.

17. The retroviral vector according to claim 16 wherein the IRES is inserted in the polypurine tract PPT located between the end of the env gene and the 5' end of the 3' LTR.

18. The retroviral vector according to claim 2 wherein the IRES is selected from the IRES elements of picornaviridae, retroviridae or retroposons or from any other RNA element capable of initiating non CAP dependent translation.

19. The retroviral vector according to claim 2 wherein the retroviral vector is based on a retrovirus selected from the group which consists of murine leukemia virus MLV, Moloney murine leukemia virus MOMLV, Akv-MLV, or SL-3-3-MLV.

20. An RNA of the retroviral vector according to claim 2.

21. A retroviral provirus produced in a target cell during a process of reverse transcription of the RNA according to claim 20.

22. An mRNA of the retroviral provirus according to claim 21.

23. A retroviral particle comprising the RNA according to claim 20.

24. A retroviral vector system for the replication of a replication-defective retroviral vector comprising the replication-defective retroviral vector according to claim 2 and a packaging cell line that synthesizes all other proteins necessary for the replication of the replication-defective retroviral vector.

25. The retroviral particle according to claim 23 obtainable from a retroviral vector system comprising the replication-defective retroviral vector and a packaging cell line that synthesizes all other proteins necessary for replication thereof or by introducing the retroviral vector or the RNA of the retroviral vector into a target cell.

26. A host cell comprising a retroviral vector according to claim 2.

27. A host cell infected with a retroviral particle according to claim 23.

28. The retroviral vector according to claim 2 or a retroviral vector system containing same or a retroviral particle containing RNA thereof or a host cell for the retroviral vector for use in introducing a heterologous gene into the genome of a mammalian cell.

* * * * *